(12) United States Patent
Xiao

(10) Patent No.: US 8,263,396 B2
(45) Date of Patent: Sep. 11, 2012

(54) METHODS AND COMPOSITIONS FOR THE PRODUCTION OF RECOMBINANT VIRUS VECTORS

(76) Inventor: Weidong Xiao, Fort Washington, PA (US)

( * ) Notice: Subject to any disclaimer, the term of this patent is extended or adjusted under 35 U.S.C. 154(b) by 177 days.

(21) Appl. No.: 12/662,165

(22) Filed: Apr. 1, 2010

(65) Prior Publication Data

US 2011/0244552 A1 Oct. 6, 2011

(51) Int. Cl.
*C12N 15/35* (2006.01)
*C12N 7/06* (2006.01)

(52) U.S. Cl. .................. 435/320.1; 435/196.1; 424/93.1

(58) Field of Classification Search ........................ None
See application file for complete search history.

(56) References Cited

U.S. PATENT DOCUMENTS

| | | | | |
|---|---|---|---|---|
| 6,759,237 B1 * | 7/2004 | Wilson et al. | .............. | 435/320.1 |
| 6,943,245 B2 * | 9/2005 | Killary et al. | ................ | 536/23.5 |
| 7,186,552 B2 * | 3/2007 | Wilson et al. | .............. | 435/320.1 |

FOREIGN PATENT DOCUMENTS

WO WO9920778 A1 * 4/1999

OTHER PUBLICATIONS

Ruffing et al. J. Virol. 1992, vol. 66, No. 12, pp. 6922-6930.*
Byung-Yoon Ahn, et al.; Identification of rpo30, a Vaccinia Virus RNA Polymerase Gene with . . . ; Molecular and Cellular Biology; Oct. 1990; pp. 5433-5441; vol. 10, No. 10.
James M. Allen, et al.; Identification and Elimination of Replication-Competent Adeno-Associated . . . ; Journal of Virology; Sep. 1997; pp. 6816-6822; vol. 71, No. 9.
Orna Elroy-Stein, et al.; Cap-independent translation of mRNA conferred by encephalomyocarditis virus 5 . . . ; Proc. Natl. Acad. Sci. USA; Aug. 1989; pp. 6126-6130; vol. 86.
Guangping Gao, et al.; Purification of Recombinant Adeno-Associated Virus Vectors by Column Chromatography and Its Performance in Vivo; Human Gene . . . ; Oct. 2000; pp. 2079-2091.
William F. Goins, et al.; Construction and Production of Recombinant Herpes Simplex Virus Vectors; Methods in Molecular Biology; pp. 97-113; vol. 433:vol. 1.
Atsushi Handa, et al.; Adeno-assoicated virus (AAV)-3-based vectors transduce haematopoietic cells not . . . ; Journal of General Virology; 2000; pp. 2077-2084.
Michael Heffernan, et al.; Polyoma and hamster paporvarius large T antigen-mediated replication of expression . . . ; Nucleic Acids Research; 1990; vol. 19, No. 1; pp. 85-92.
James G. Keck, et al.; Role of DNA Replication in Vaccinia Virus Gene Expression: A Naked Template . . . ; Cell; 1990; vol. 61; pp. 801-809.
G. Marzio, et al.; A replication-competent adenovirus assay for E1-deleted Ad35 vectors . . . ; ScienceDirect; 2007; pp. 2228-2237.
Maryellen Polvino-Bodnar, et al.; DNA Binding Activity Is Required for EBNA 1-Dependent Transcriptional Activation and DNA . . . ; Virology, 1992; vol. 187; pp. 591-603.
Jacky F. C. Schmitt, et al.; Sequence and Transcriptional Analysis of the Vaccinia Virus Hindlll I Fragment; Journal of Virology; Jun. 1988; pp. 1889-1897.
Tatiana G. Senkevich, et al.; The Genome of Molluscum Contagiosum Virus: Analysis and Comparison with Other Poxviruses; Virology; 1997; vol. 233; pp. 19-42.
George A. Ward, et al.; Stringent chemical and thermal regulation of recombinant gene expression by vaccinia . . . ; Pro. Natl. Acad. Sci. USA; Jul. 1995; vol. 92; pp. 6773-6777.
Riccardo Wittek, et al.; Mapping of a Gene Coding for a Major Late Structural Polypeptide . . . ; Journal of Virology; Feb. 1984; pp. 371-378.
Riccardo Wittek, et al.; Mapping of Genes Coding for the two major vaccinia virus core polypeptides; Nucleic Acids Research; 1984; vol. 12, No. 12; pp. 4835-4848.
Annick Brandenburger, et al.; Influence of Sequence and Size of DNA on Packaging Efficiency of Parvovirus MVM-Based Vectors; Human Gene Therapy; May 1999; 10; pp. 1229-1238.

* cited by examiner

*Primary Examiner* — Bao Li
(74) *Attorney, Agent, or Firm* — Andrews Kurth LLP; Michael Ye

(57) ABSTRACT

A method for the production of a replication-deficient recombinant virus vector is disclosed. The replication-deficient recombinant virus vector has a recombinant virus genome with one or more defective viral genes. The method comprises infecting a host cell with a carrier virus having a carrier virus genome encoding one or more trans factors or variants thereof, incubating the infected host cell for a desired period of time, and isolating the replication-deficient recombinant virus vector. The carrier virus is a cytoplasmic virus that retains the carrier virus genome in the cytoplasm of the host cell. The host cell contains the recombinant viral genome and retains the recombinant viral genome in a nucleus of the host cell. Also disclosed is a carrier virus for the production of a replication-deficient recombinant virus vector.

12 Claims, 11 Drawing Sheets

SEQUENCE LISTING

<160> NUMBER OF SEQ ID NOS: 16

<210> SEQ ID NO 1
<211> LENGTH: 39
<212> TYPE: DNA
<213> ORGANISM: Vaccinia virus

<400> SEQUENCE: 1
aaaaattgaa attttatttt ttttttttgg aatataaat                      39

<210> SEQ ID NO 2
<211> LENGTH: 1963
<212> TYPE: DNA
<213> ORGANISM: Artificial Sequence
<220> FEATURE:
<223> OTHER INFORMATION: expression cassette

<400> SEQUENCE: 2
aaaaattgaa attttatttt ttttttttgg aatataaata aggaattcct gcaggctagc    60
cccgggaagc ttccatgccg gggttttacg agattgtgat taaggtcccc agcgaccttg   120
acgagcatct gcccggcatt tctgacagct tgtgaactg ggtggccgag aaggaatggg    180
agttgccgcc agattctgac atggatctga atctgattga gcaggcaccc ctgaccgtgg   240
ccgagaagct gcagcgcgac tttctgacgg aatggcgccg tgtgagtaag gccccggagg   300
cccttttctt tgtgcaattt gagaagggag agagctactt ccacatgcac gtgctcgtgg   360
aaaccaccgg ggtgaaatcc atggttttgg gacgtttcct gagtcagatt cgcgaaaaac   420
tgattcagag aatttaccgc gggatcgagc cgactttgcc aaactggttc gcggtcacaa   480
agaccagaaa tggcgccgga ggcgggaaca aggtggtgga tgagtgctac atccccaatt   540
acttgctccc caaaacccag cctgagctcc agtgggcgtg gactaatatg aacagtatt    600 taagcgcctg tttgaatctc acggagcgta acgggttggt ggcgcagcat ctgacgcacg   660
tgtcgcagac gcaggagcag aacaaagaga atcagaatcc caattctgat gcgccggtga   720
tcagatcaaa aacttcagcc aggtacatgg agctggtcgg gtggctcgtg acaaggggga   780
ttacctcgga gaagcagtgg atccaggagg accaggcctc atacatctcc ttcaatgcgg   840
cctccaactc gcggtcccaa atcaaggctg ccttggacaa tgcgggaaag attatgagcc   900
tgactaaaac cgcccccgac tacctggtgg gccagcagcc cgtggaggac atttccagca   960
atcggattta taaatttttg gaactaaacg ggtacgatcc ccaatatgcg gcttccgtct  1020
ttctgggatg ggccacgaaa agttcggca agaggaacac catctggctg tttgggcctg   1080
caactaccgg gaagaccaac atcgcggagg ccatagccca cactgtgccc ttctacgggt  1140
gcgtaaactg gaccaatgag aactttccct caacgactg tgtcgacaag atggtgatct   1200
ggtgggagga gggaagatg accgccaagg tcgtggagtc ggccaaagcc attctcggag   1260
gaagcaaggt gcgcgtggac cagaaatgca gtcctcggc ccagatagac ccgactcccg    1320
tgatcgtcac ctccaacacc aacatgtgcg ccgtgattga cgggaactca acgaccttcg   1380
aacaccagca gccgttgcaa gaccggatgt tcaaatttga actcacccgc cgtctggatc  1440
atgactttgg gaaggtcacc aagcaggaag tcaaagactt tttccggtgg gcaaaggatc   1500
acgtggttga ggtggagcat gaattctacg tcaaaaaggg tggagccaag aaaagacccg  1560
cccccagtga cgcagatata agtgagccca acgggtgcg cgagtcagtt gcgcagccat   1620
cgacgtcaga cgcggaagct tcgatcaact acgcagacag gtaccaaaac aaatgttctc   1680

| | |
|---|---|
| gtcacgtggg catgaatctg atgctgtttc cctgcagaca atgcgagaga atgaatcaga | 1740 |
| attcaaatat ctgcttcact cacggacaga aagactgttt agagtgcttt cccgtgtcag | 1800 |
| aatctcaacc cgtttctgtc gtcaaaaagg cgtatcagaa actgtgctac attcatcata | 1860 |
| tcatgggaaa ggtgccagac gcttgcactg cctgcgatct ggtcaatgtg gatttggatg | 1920 |
| actgcatctt tgaacaataa aggcctaaat aaataatttt tat | 1963 |

<210> SEQ ID NO 3
<211> LENGTH: 2029
<212> TYPE: DNA
<213> ORGANISM: Artificial Sequence
<220> FEATURE:
<223> OTHER INFORMATION: expression cassette

<400> SEQUENCE: 3

| | |
|---|---|
| aaaaattgaa attttatttt ttttttttgg aatataaata aggaattcct gcaggctagc | 60 |
| cccgggaagc ttccatgccg gggttttacg agattgtgat taaggtcccc agcgaccttg | 120 |
| acgagcatct gcccggcatt tctgacagct tgtgaactg ggtggccgag aaggaatggg | 180 |
| agttgccgcc agattctgac atggatctga atctgattga gcaggcaccc ctgaccgtgg | 240 |
| ccgagaagct gcagcgcgac tttctgacgg aatggcgccg tgtgagtaag gccccggagg | 300 |
| cccttttctt tgtgcaattt gagaaggag agagctactt ccacatgcac gtgctcgtgg | 360 |
| aaaccaccgg ggtgaaatcc atggttttgg gacgtttcct gagtcagatt cgcgaaaaac | 420 |
| tgattcagag aatttaccgc gggatcgagc cgactttgcc aaactggttc gcggtcacaa | 480 |
| agaccagaaa tggcgccgga ggcgggaaca aggtggtgga tgagtgctac atccccaatt | 540 |
| acttgctccc caaaacccag cctgagctcc agtgggcgtg gactaatatg gaacagtatt | 600 |
| taagcgcctg tttgaatctc acggagcgta acggttggt ggcgcagcat ctgacgcacg | 660 |
| tgtcgcagac gcaggagcag aacaaagaga atcagaatcc caattctgat gcgccggtga | 720 |
| tcagatcaaa aacttcagcc aggtacatgg agctggtcgg gtggctcgtg acaaggggga | 780 |
| ttacctcgga gaagcagtgg atccaggagg accaggcctc atacatctcc ttcaatgcgg | 840 |
| cctccaactc gcggtcccaa atcaaggctg ccttggacaa tgcgggaaag attatgagcc | 900 |
| tgactaaaac cgccccgac tacctggtgg gccagcagcc cgtggaggac atttccagca | 960 |
| atcggattta taaatttttg gaactaaacg ggtacgatcc ccaatatgcg gcttccgtct | 1020 |
| ttctgggatg ggccacgaaa aagttcggca agaggaacac catctggctg tttgggcctg | 1080 |
| caactaccgg gaagaccaac atcgcggagg ccatagccca cactgtgccc ttctacgggt | 1140 |
| gcgtaaactg gaccaatgag aactttcct tcaacgactg tgtcgacaag atggtgatct | 1200 |
| ggtgggagga gggaagatg accgccaagg tcgtggagtc ggccaaagcc attctcggag | 1260 |
| gaagcaaggt gcgcgtggac cagaaatgca gtcctcggc ccagatagac ccgactcccg | 1320 |
| tgatcgtcac ctccaacacc aacatgtgcg ccgtgattga cggaactca acgaccttcg | 1380 |
| aacaccagca gccgttgcaa gaccggatgt tcaaatttga actcacccgc cgtctggatc | 1440 |
| atgactttgg gaaggtcacc aagcaggaag tcaaagactt tttccggtgg gcaaaggatc | 1500 |
| acgtggttga ggtggagcat gaattctacg tcaaaaaggg tggagccaag aaaagacccg | 1560 |
| cccccagtga cgcagatata agtgagccca acgggtgcg cgagtcagtt gcgcagccat | 1620 |
| cgacgtcaga cgcggaagct tcgatcaact acgcagacag gtaccaaaac aaatgttctc | 1680 |
| gtcacgtggg catgaatctg atgctgtttc cctgcagaca atgcgagaga atgaatcaga | 1740 |
| attcaaatat ctgcttcact cacggacaga aagactgttt agagtgcttt cccgtgtcag | 1800 |

```
aatctcaacc cgtttctgtc gtcaaaaagg cgtatcagaa actgtgctac attcatcata   1860
tcatgggaaa ggtgccagac gcttgcactg cctgcgatct ggtcaatgtg gatttggatg   1920
actgcatctt tgaacaataa atgatttaaa tcaggtatgg ctgccgatgg ttatcttcca   1980
gattggctcg aggacactct ctctgaaggc ctaaataaat aattttat                2029
```

<210> SEQ ID NO 4
<211> LENGTH: 1291
<212> TYPE: DNA
<213> ORGANISM: Artificial Sequence
<220> FEATURE:
<223> OTHER INFORMATION: expression cassette

<400> SEQUENCE: 4

```
aaaaattgaa attttatttt ttttttttgg aatataaata aggaattcct gcaggctagc     60
cccgggaagc ttccatggag ctggtcgggt ggctcgtgga caaggggatt acctcggaga    120
agcagtggat ccaggaggac caggcctcat acatctcctt caatgcggcc tccaactcgc    180
ggtcccaaat caaggctgcc ttggacaatg cgggaaagat tatgagcctg actaaaaccg    240
cccccgacta cctggtgggc cagcagcccg tggaggactt ccagcaat cggatttata    300 aaattttgga actaaacggg tacgatcccc aatatgcggc ttccgtcttt ctgggatggg    360
ccacgaaaaa gttcggcaag aggaacacca tctggctgtt tgggcctgca actaccggga    420
agaccaacat cgcggaggcc atagcccaca ctgtgcccct ctacgggtgc gtaaactgga    480
ccaatgagaa ctttcccttc aacgactgtg tcgacaagat ggtgatctgg tgggaggagg    540
ggaagatgac cgccaaggtc gtggagtcgg ccaaagccat tctcggagga agcaaggtgc    600
gcgtggacca gaaatgcaag tcctcggccc agatagaccc gactcccgtg atcgtcacct    660
ccaacaccaa catgtgcgcc gtgattgacg ggaactcaac gaccttcgaa caccagcagc    720
cgttgcaaga ccggatgttc aaatttgaac tcacccgccg tctggatcat gactttggga    780
aggtcaccaa gcaggaagtc aaagactttt tccgtgggc aaaggatcac gtggttgagg    840
tggagcatga attctacgtc aaaaaggtg gagccaagaa aagacccgcc ccagtgacg    900 cagatataag tgagcccaaa cgggtgcgcg agtcagttgc gcagccatcg acgtcagacg    960
cggaagcttc gatcaactac gcagacaggt accaaaacaa atgttctcgt cacgtgggca   1020
tgaatctgat gctgtttccc tgcagacaat gcgagagaat gaatcagaat tcaaatatct   1080
gcttcactca cggacagaaa gactgtttag agtgctttcc cgtgtcagaa tctcaacccg   1140
tttctgtcgt caaaaaggcg tatcagaaac tgtgctacat tcatcatatc atgggaaagg   1200
tgccagacgc ttgcactgcc tgcgatctgg tcaatgtgga tttggatgac tgcatctttg   1260
aacaataaag gcctaaataa ataatttta t                                   1291
```

<210> SEQ ID NO 5
<211> LENGTH: 1357
<212> TYPE: DNA
<213> ORGANISM: Artificial Sequence
<220> FEATURE:
<223> OTHER INFORMATION: expression cassette

<400> SEQUENCE: 5

```
aaaaattgaa attttatttt ttttttttgg aatataaata aggaattcct gcaggctagc     60
cccgggaagc ttccatggag ctggtcgggt ggctcgtgga caaggggatt acctcggaga    120
agcagtggat ccaggaggac caggcctcat acatctcctt caatgcggcc tccaactcgc    180
ggtcccaaat caaggctgcc ttggacaatg cgggaaagat tatgagcctg actaaaaccg    240
```

```
cccccgacta cctggtgggc cagcagcccg tggaggacat ttccagcaat cggatttata    300
aaattttgga actaaacggg tacgatcccc aatatgcggc ttccgtcttt ctgggatggg    360
ccacgaaaaa gttcggcaag aggaacacca tctggctgtt tgggcctgca actaccggga    420
agaccaacat cgcggaggcc atagcccaca ctgtgcccct ctacgggtgc gtaaactgga    480
ccaatgagaa cttcccttc aacgactgtg tcgacaagat ggtgatctgg tgggaggagg     540
ggaagatgac cgccaaggtc gtggagtcgg ccaaagccat tctcggagga agcaaggtgc    600
gcgtggacca gaaatgcaag tcctcggccc agatagaccc gactcccgtg atcgtcacct    660
ccaacaccaa catgtgcgcc gtgattgacg ggaactcaac gaccttcgaa caccagcagc    720
cgttgcaaga ccggatgttc aaatttgaac tcacccgccg tctggatcat gactttggga    780
aggtcaccaa gcaggaagtc aaagactttt tccggtgggc aaaggatcac gtggttgagg    840
tggagcatga attctacgtc aaaaagggtg agccaagaa aagacccgcc cccagtgacg     900
cagatataag tgagcccaaa cgggtgcgcg agtcagttgc gcagccatcg acgtcagacg    960
cggaagcttc gatcaactac gcagacaggt accaaaacaa atgttctcgt cacgtgggca   1020
tgaatctgat gctgtttccc tgcagacaat gcgagagaat gaatcagaat tcaaatatct   1080
gcttcactca cggacagaaa gactgtttag agtgctttcc cgtgtcagaa tctcaacccg   1140
tttctgtcgt caaaaaggcg tatcagaaac tgtgctacat tcatcatatc atgggaaagg   1200
tgccagacgc ttgcactgcc tgcgatctgg tcaatgtgga tttggatgac tgcatctttg   1260
aacaataaat gatttaaatc aggtatggct gccgatggtt atcttccaga ttggctcgag   1320
gacactctct ctgaaggcct aaataaataa tttttat                            1357

<210> SEQ ID NO 6
<211> LENGTH: 2291
<212> TYPE: DNA
<213> ORGANISM: Artificial Sequence
<220> FEATURE:
<223> OTHER INFORMATION: expression cassette

<400> SEQUENCE: 6
aaaaattgaa attttatttt ttttttttgg aatataaata aggaattcct gcaggctagc     60
cccatggctg ccgatggtta tcttccagat tggctcgagg acactctctc tgaaggaata    120
agacagtggt ggaagctcaa acctggccca ccaccaccaa gcccgcagag cggcataag     180 gacgacagca ggggtcttgt gcttcctggg tacaagtacc tcggacccct caacggactc    240 gacaaggag agccggtcaa cgaggcagac gccgcgccc tcgagcacga caaagcctac     300
gaccggcagc tcgacagcgg agacaacccg tacctcaagt acaaccacgc cgacgcggag    360
tttcaggagc gccttaaaga agatacgtct ttgggggca acctcggacg agcagtcttc    420
caggcgaaaa agagggttct tgaacctctg ggcctggttg aggaacctgt taagacggct    480
ccgggaaaaa gaggccggt agagcactct cctgtggagc cagactcctc ctcgggaacc    540
ggaaaggcgg gccagcagcc tgcaagaaaa agattgaatt ttggtcagac tggagacgca    600
gactcagtac ctgaccccca gcctctcgga cagccaccag cagccccctc tggtctggga    660
actaatacga tggctacagg cagtggcgca ccaatggcag acaataacga gggcgccgac    720
ggagtgggta attcctcggg aaattggcat tgcgattcca catggatggg cgacagagtc    780
atcaccacca gcacccgaac ctgggccctg cccacctaca acaaccacct ctacaaacaa    840
atttccagcc aatcaggagc ctcgaacgac aatcactact ttggctacag caccccttgg    900
gggtattttg acttcaacag attccactgc cacttttcac cacgtgactg gcaaagactc    960
```

```
atcaacaaca actggggatt ccgacccaag agactcaact tcaagctctt taacattcaa    1020
gtcaaagagg tcacgcagaa tgacggtacg acgacgattg ccaataacct taccagcacg    1080
gttcaggtgt ttactgactc ggagtaccag ctcccgtacg tcctcggctc ggcgcatcaa    1140
ggatgcctcc cgccgttccc agcagacgtc ttcatggtgc cacagtatgg atacctcacc    1200
ctgaacaacg ggagtcaggc agtaggacgc tcttcatttt actgcctgga gtactttcct    1260
tctcagatgc tgcgtaccgg aaacaacttt accttcagct cacttttga ggacgttcct     1320 ttccacagca gctacgctca gccagagtg ctggaccgtc tcatgaatcc tctcatcgac     1380
cagtacctgt attacttgag cagaacaaac actccaagtg aaccaccac gcagtcaagg     1440 cttcagttttt ctcaggccgg agcgagtgac attcgggacc agtctaggaa ctggcttcct    1500
ggaccctgtt accgccagca gcgagtatca agacatctg cggataacaa caacagtgaa      1560
tactcgtgga ctggagctac caagtaccac ctcaatggca gagactctct ggtgaatccg     1620 ggccccggcca tggcaagcca aaggacgat gaagaaaagt ttttcctca gagcggggtt      1680 ctcatctttg gaagcaagg ctcagagaaa acaaatgtgg acattgaaaa ggtcatgatt      1740
acagacgaag aggaaatcag gacaaccaat cccgtggcta cggagcagta tggttctgta    1800
tctaccaacc tccagagagg caacagacaa gcagctaccg cagatgtcaa cacacaaggc    1860
gttcttccag gcatggtctg gcaggacaga gatgtgtacc ttcaggggcc catctgggca    1920
aagattccac acacggacgg acattttcac ccctctcccc tcatgggtgg attcggactt    1980
aaacaccctc ctcccacagat tctcatcaag aacacccgg tacctgcgaa tccttcgacc    2040
accttcagtg cggcaaagtt tgcttccttc atcacacagt actccacggg acaggtcagc    2100
gtggagatcg agtgggagct gcagaaggaa acagcaaac gctggaatcc cgaaattcag    2160
tacacttcca actacaacaa gtctgttaat gtggacttta ctgtgacac taatggcgtg      2220 tattcagagc ctcgccccat tggcaccaga tacctgactc gtaatctgta acctaaataa    2280
ataattttta t                                                          2291

<210> SEQ ID NO 7
<211> LENGTH: 1880
<212> TYPE: DNA
<213> ORGANISM: Artificial Sequence
<220> FEATURE:
<223> OTHER INFORMATION: expression cassette

<400> SEQUENCE: 7
aaaaattgaa attttatttt ttttttttgg aatataaata aggaattcct gcaggctagc      60
cccacggctc cgggaaaaaa gaggccggta gagcactctc ctgtggagcc agactcctcc    120
tcgggaaccg gaaaggcggg ccagcagcct gcaagaaaaa gattgaattt tggtcagact    180
ggagacgcag actcagtacc tgaccccag cctctcggac agccaccagc agcccctct      240 ggtctgggaa ctaatacgat ggctacaggc agtggcgcac caatggcaga caataacgag    300
ggcgccgacg gagtgggtaa ttcctcggga aattggcatt gcgattccac atggatgggc    360
gacagagtca tcaccaccag caccgaacc tgggccctgc ccacctacaa caaccacctc    420
tacaaacaaa tttccagcca atcaggagcc tcgaacgaca atcactactt tggctacagc    480
accccttggg ggtattttga cttcaacaga ttccactgcc actttcacc acgtgactgg    540 caaagactca tcaacaacaa ctggggattc cgacccaaga gactcaactt caagctcttt    600
aacattcaag tcaaagaggt cacgcagaat gacggtacga cgacgattgc caataacctt    660
accagcacgg ttcaggtgtt tactgactcg gagtaccagc tcccgtacgt cctcggctcg    720
```

```
gcgcatcaag gatgcctccc gccgttccca gcagacgtct tcatggtgcc acagtatgga    780
tacctcaccc tgaacaacgg gagtcaggca gtaggacgct cttcatttta ctgcctggag    840
tactttcctt ctcagatgct gcgtaccgga acaactttta ccttcagcta cactttgag    900
gacgttcctt tccacagcag ctacgctcac agccagagtc tggaccgtct catgaatcct    960
ctcatcgacc agtacctgta ttacttgagc agaacaaaca ctccaagtgg aaccaccacg   1020
cagtcaaggc ttcagttttc tcaggccgga gcgagtgaca ttcgggacca gtctaggaac   1080
tggcttcctg gaccctgtta ccgccagcag cgagtatcaa agacatctgc ggataacaac   1140
aacagtgaat actcgtggac tggagctacc aagtaccacc tcaatggcag agactctctg   1200
gtgaatccgg gcccggccat ggcaagccac aaggacgatg aagaaaagtt ttttcctcag   1260
agcggggttc tcatctttgg gaagcaaggc tcagagaaaa caaatgtgga cattgaaaag   1320
gtcatgatta cagacgaaga ggaaatcagg acaaccaatc ccgtggctac ggagcagtat   1380
ggttctgtat ctaccaacct ccagagaggc aacagacaag cagctaccgc agatgtcaac   1440
acacaaggcg ttcttccagg catggtctgg caggacagag atgtgtacct tcaggggccc   1500
atctgggcaa agattccaca cacggacgga cattttcacc cctctcccct catgggtgga   1560
ttcggactta aacaccctcc tccacagatt ctcatcaaga cacccggt acctgcgaat   1620
ccttcgacca ccttcagtgc ggcaaagttt gcttccttca tcacacagta ctccacggga   1680
caggtcagcg tggagatcga gtgggagctg cagaaggaaa acagcaaacg ctggaatccc   1740
gaaattcagt acacttccaa ctacaacaag tctgttaatg tggactttac tgtggacact   1800
aatggcgtgt attcagagcc tcgccccatt ggcaccagat acctgactcg taatctgtaa   1860
cctaaataaa taattttat                                                 1880

<210> SEQ ID NO 8
<211> LENGTH: 1699
<212> TYPE: DNA
<213> ORGANISM: Artificial Sequence
<220> FEATURE:
<223> OTHER INFORMATION: expression cassette

<400> SEQUENCE: 8
aaaaattgaa attttatttt tttttttgg aatataaata aggaattcct gcaggctagc     60
cccgggaagc ttccatggct acaggcagtg gcgcaccaat ggcagacaat aacgagggcg    120
ccgacggagt gggtaattcc tcgggaaatt ggcattgcga ttccacatgg atgggcgaca    180
gagtcatcac caccagcacc cgaacctggg ccctgcccac ctacaacaac cacctctaca    240
aacaaatttc cagccaatca ggagcctcga acgacaatca ctactttggc tacagcaccc    300
cttggggta tttgacttc aacagattcc actgccactt tcaccacgt gactggcaaa       360
gactcatcaa caacaactgg ggattccgac ccaagagact caacttcaag ctctttaaca    420
ttcaagtcaa agaggtcacg cagaatgacg gtacgacgac gattgccaat aaccttacca    480
gcacggttca ggtgtttact gactcggagt accagctccc gtacgtcctc ggctcggcgc    540
atcaaggatg cctcccgccg ttcccagcag acgtcttcat ggtgccacag tatggatacc    600
tcaccctgaa caacgggagt caggcagtag gacgctcttc attttactgc ctggagtact    660
tccttctca gatgctgcgt accggaaaca actttacctt cagctacact tttgaggacg    720
ttccttttcca cagcagctac gctcacagcc agagtctgga ccgtctcatg aatcctctca    780
tcgaccagta cctgtattac ttgagcagaa caaacactcc aagtggaacc accacgcagt    840
caaggcttca gttttctcag gccggagcga gtgacattcg ggaccagtct aggaactggc    900
```

```
ttcctggacc ctgttaccgc cagcagcgag tatcaaagac atctgcggat aacaacaaca    960
gtgaatactc gtggactgga gctaccaagt accacctcaa tggcagagac tctctggtga   1020
atccgggccc ggccatggca agccacaagg acgatgaaga aaagttttt cctcagagcg    1080 gggttctcat ctttgggaag caaggctcag agaaaacaaa tgtggacatt gaaaaggtca   1140
tgattacaga cgaagaggaa atcaggacaa ccaatcccgt ggctacggag cagtatggtt   1200
ctgtatctac caacctccag agaggcaaca gacaagcagc taccgcagat gtcaacacac   1260
aaggcgttct tccaggcatg gtctggcagg acagagatgt gtaccttcag ggcccatct    1320 gggcaaagat tccacacacg gacggacatt ttcaccctc tccctcatg ggtggattcg     1380 gacttaaaca ccctcctcca cagattctca tcaagaacac cccggtacct gcgaatcctt   1440
cgaccacctt cagtgcggca aagtttgctt ccttcatcac acagtactcc acgggacagg   1500
tcagcgtgga gatcgagtgg gagctgcaga aggaaaacag caaacgctgg aatcccgaaa   1560
ttcagtacac ttccaactac aacaagtctg ttaatgtgga cttactgtg gacactaatg    1620 gcgtgtattc agagcctcgc cccattggca ccagataccct gactcgtaat ctgtaaaggc   1680
ctaaataaat aatttttat                                                1699

<210> SEQ ID NO 9
<211> LENGTH: 1083
<212> TYPE: DNA
<213> ORGANISM: Artificial Sequence
<220> FEATURE:
<223> OTHER INFORMATION: expression cassette

<400> SEQUENCE: 9
aaaaattgaa attttatttt ttttttttgg aatataaata aggaattcct gcaggctagc     60
cccgggaagc ttcatgaga catattatct gccacggagg tgttattacc gaagaaatgg    120
ccgccagtct tttggaccag ctgatcgaag aggtactggc tgataatctt ccacctccta   180
gccattttga accacctacc cttcacgaac tgtatgattt agacgtgacg gcccccgaag   240
atcccaacga ggaggcggtt tcgcagattt ttcccgactc tgtaatgttg gcggtgcagg   300
aagggattga cttactcact ttccgccgg cgccggttc tccggagccg cctcacctt     360 cccggcagcc cgagcagccg gagcagagag ccttgggtcc ggtttctatg ccaaaccttg    420
taccggaggt gatcgatctt acctgccacg aggctggctt tccacccagt gacgacgagg   480
atgaagaggg tgaggagttt gtgttagatt atgtggagca ccccgggcac ggttgcaggt   540
cttgtcatta tcaccggagg aatacggggg acccagatat tatgtgttcg ctttgctata   600
tgaggacctg tggcatgttt gtctacagta agtgaaaatt atgggcagtg ggtgatagag   660
tggtgggttt ggtgtggtaa tttttttttt aattttaca gttttgtggt ttaaagaatt    720
ttgtattgtg atttttttaa aaggtcctgt gtctgaacct gagcctgagc ccgagccaga   780
accggagcct gcaagaccta cccgccgtcc taaaatggcg cctgctatcc tgagacgccc   840
gacatcacct gtgtctagag aatgcaatag tagtacggat agctgtgact ccggtccttc   900
taacacacct cctgagatac acccggtggt cccgctgtgc cccattaaac cagttgccgt   960
gagagttggt gggcgtcgcc aggctgtgga atgtatcgag acttgctta acgagcctgg   1020 gcaacctttg gacttgagct gtaaacgccc caggccataa aggcctaaat aaataatttt   1080
tat                                                                 1083

<210> SEQ ID NO 10
<211> LENGTH: 1588
<212> TYPE: DNA
```

<213> ORGANISM: Artificial Sequence
<220> FEATURE:
<223> OTHER INFORMATION: expression cassette

<400> SEQUENCE: 10

```
aaaaattgaa attttatttt ttttttttgg aatataaata aggaattcct gcaggctagc      60
cccgggaagc ttccatggag cgaagaaacc catctgagcg gggggtacct gctggatttt     120
ctggccatgc atctgtggag agcggttgtg agacacaaga atcgcctgct actgttgtct     180
tccgtccgcc cggcgataat accgacggag gagcagcagc agcagcagga ggaagccagg     240
cggcggcggc aggagcagag cccatggaac ccgagagccg gcctggaccc tcgggaatga     300
atgttgtaca ggtggctgaa ctgtatccag aactgagacg cattttgaca attacagagg     360
atgggcaggg gctaaagggg gtaaagaggg agcgggggc ttgtgaggct acagaggagg      420
ctaggaatct agcttttagc ttaatgacca gacaccgtcc tgagtgtatt acttttcaac     480
agatcaagga taattgcgct aatgagcttg atctgctggc gcagaagtat tccatagagc     540
agctgaccac ttactggctg cagccagggg atgattttga ggaggctatt agggtatatg     600
caaaggtggc acttaggcca gattgcaagt acaagatcag caaacttgta aatatcagga     660
attgttgcta catttctggg aacggggccg aggtggagat agatacggag gatagggtgg     720
cctttagatg tagcatgata aatatgtggc gggggtgct tggcatggac ggggtggtta      780
ttatgaatgt aaggtttact ggccccaatt ttagcggtac ggttttcctg gccaatacca     840
accttatcct acacggtgta agcttctatg gtttaacaa tacctgtgtg gaagcctgga      900
ccgatgtaag ggttcggggc tgtgcctttt actgctgctg aaggggggtg gtgtgtcgcc     960
ccaaaagcag ggcttcaatt aagaaatgcc tctttgaaag gtgtaccttg ggtatcctgt    1020
ctgagggtaa ctccagggtg cgccacaatg tggcctccga ctgtggttgc ttcatgctag    1080
tgaaaagcgt ggctgtgatt aagcataaca tggtatgtgg caactgcgag gcagggcct     1140
ctcagatgct gacctgctcg gacggcaact gtcacctgct gaagaccatt cacgtagcca    1200
gccactctcg caaggcctgg ccagtgtttg agcataacat actgacccgc tgttccttgc    1260
atttgggtaa caggagggg gtgttcctac cttaccaatg caatttgagt cacactaaga     1320
tattgcttga gcccgagagc atgtccaagg tgaacctgaa cggggtgttt gacatgacca    1380
tgaagatctg gaaggtgctg aggtacgatg agacccgcac caggtgcaga ccctgcgagt    1440
gtggcggtaa acatattagg aaccagcctg tgatgctgga tgtgaccgag gagctgaggc    1500
ccgatcactt ggtgctggcc tgcacccgcg ctgagtttgg ctctagcgat gaagatacag    1560
attgaaggcc taaataaata attttat                                         1588
```

<210> SEQ ID NO 11
<211> LENGTH: 1687
<212> TYPE: DNA
<213> ORGANISM: Artificial Sequence
<220> FEATURE:
<223> OTHER INFORMATION: expression cassette

<400> SEQUENCE: 11

```
aaaaattgaa attttatttt ttttttttgg aatataaata aggaattcct gcaggctagc      60
cccgggaagc ttccatggcc agtcgggaag aggagcagcg cgaaaccacc cccgagcgcg     120
gacgcggtgc ggcgcgacgt cccccaacca tggaggacgt gtcgtccccg tccccgtcgc    180
cgccgcctcc ccgggcgccc caaaaaaagc ggatgaggcg gcgtatcgag tccgaggacg     240
aggaagactc atcacaagac gcgctggtgc cgcgcacacc cagcccgcgg ccatcgacct     300
```

| | |
|---|---|
| cggcggcgga tttggccatt gcgcccaaga agaaaaagaa gcgcccttct cccaagcccg | 360 |
| agcgcccgcc atcaccagag gtaatcgtgg acagcgagga gaaagagaa gatgtggcgc | 420 |
| tacaaatggt gggtttcagc aacccaccgg tgctaatcaa gcatggcaaa ggaggtaagc | 480 |
| gcacagtgcg gcggctgaat gaagacgacc cagtggcgcg tggtatgcgg acgcaagagg | 540 |
| aagaggaaga gcccagcgaa gcggaaagtg aaattacggt gatgaacccg ctgagtgtgc | 600 |
| cgatcgtgtc tgcgtgggag aagggcatgg aggctgcgcg cgcgctgatg gacaagtacc | 660 |
| acgtggataa cgatctaaag gcgaacttca aactactgcc tgaccaagtg gaagctctgg | 720 |
| cggccgtatg caagacctgg ctgaacgagg agcaccgcgg gttgcagctg accttcacca | 780 |
| gcaacaagac ctttgtgacg atgatggggc gattcctgca ggcgtacctg cagtcgtttg | 840 |
| cagaggtgac ctacaagcat cacgagccca cgggctgcgc gttgtggctg caccgctgcg | 900 |
| ctgagatcga aggcgagctt aagtgtctac acggaagcat tatgataaat aaggagcacg | 960 |
| tgattgaaat ggatgtgacg agcgaaaacg ggcagcgcgc gctgaaggag cagtctagca | 1020 |
| aggccaagat cgtgaagaac cggtggggcc gaaatgtggt gcagatctcc aacaccgacg | 1080 |
| caaggtgctg cgtgcacgac gcggcctgtc cggccaatca gttttccggc aagtcttgcg | 1140 |
| gcatgttctt ctctgaaggc gcaaaggctc aggtggcttt taagcagatc aaggctttta | 1200 |
| tgcaggcgct gtatcctaac gcccagaccg ggcacggtca cctttttgatg ccactacggt | 1260 |
| gcgagtgcaa ctcaaagcct gggcacgcgc ccttttttggg aaggcagcta ccaaagttga | 1320 |
| ctccgttcgc cctgagcaac gcggaggacc tggacgcgga tctgatctcc gacaagagcg | 1380 |
| tgctggccag cgtgcaccac ccggcgctga tagtgttcca gtgctgcaac cctgtgtatc | 1440 |
| gcaactcgcg cgcgcagggc ggaggcccca actgcgactt caagatatcg gcgcccgacc | 1500 |
| tgctaaacgc gttggtgatg gtgcgcagcc tgtggagtga aaacttcacc gagctgccgc | 1560 |
| ggatggttgt gcctgagttt aagtggagca ctaaacacca gtatcgcaac gtgtccctgc | 1620 |
| cagtggcgca tagcgatgcg cggcagaacc cctttgattt ttaaaggcct aaataaataa | 1680 |
| tttttat | 1687 |

<210> SEQ ID NO 12
<211> LENGTH: 982
<212> TYPE: DNA
<213> ORGANISM: Artificial Sequence
<220> FEATURE:
<223> OTHER INFORMATION: expression cassette

<400> SEQUENCE: 12

| | |
|---|---|
| aaaaattgaa attttatttt ttttttttgg aatataaata aggaattcct gcaggctagc | 60 |
| cccgggaagc ttccatgact acgtccggcg ttccatttgg catgacacta cgaccaacac | 120 |
| gatctcggtt gtctcggcgc actccgtaca gtagggatcg tctacctcct tttgagacag | 180 |
| aaacccgcgc taccatactg gaggatcatc cgctgctgcc cgaatgtaac actttgacaa | 240 |
| tgcacaacgt gagttacgtg cgaggtcttc cctgcagtgt gggatttacg ctgattcagg | 300 |
| aatgggttgt tccctgggat atggttctaa cgcggggaga gcttgtaatc ctgaggaagt | 360 |
| gtatgcacgt gtgcctgtgt tgtgccaaca ttgatatcat gacgagcatg atgatccatg | 420 |
| gttacgagtc ctgggctctc cactgtcatt gttccagtcc cggttccctg cagtgtatag | 480 |
| ccggcgggca ggttttggcc agctggttta ggatggtggt ggatggcgcc atgtttaatc | 540 |
| agaggtttat atggtaccgg gaggtggtga attacaacat gccaaagag gtaatgttta | 600 |
| tgtccagcgt gtttatgagg ggtcgccact taatctacct gcgcttgtgg tatgatggcc | 660 |

-continued

| | |
|---|---|
| acgtgggttc tgtggtcccc gccatgagct ttggatacag cgccttgcac tgtgggattt | 720 |
| tgaacaatat tgtggtgctg tgctgcagtt actgtgctga tttaagtgag atcagggtgc | 780 |
| gctgctgtgc ccggaggaca aggcgcctta tgctgcgggc ggtgcgaatc atcgctgagg | 840 |
| agaccactgc catgttgtat tcctgcagga cggagcggcg gcggcagcag tttattcgcg | 900 |
| cgctgctgca gcaccaccgc cctatcctga tgcacgatta tgactctacc cccatgtaga | 960 |
| ggcctaaata aataattttt at | 982 |

```
<210> SEQ ID NO 13
<211> LENGTH: 3994
<212> TYPE: DNA
<213> ORGANISM: Artificial Sequence
<220> FEATURE:
<223> OTHER INFORMATION: expression cassette

<400> SEQUENCE: 13
```

| | |
|---|---|
| aaaaattgaa atttattttt ttttttttgg aatataaata aggaattcct gcaggctagc | 60 |
| cccgggaagc ttccatggcg tcggagaaca agcagcgccc cggctccccg ggccccaccg | 120 |
| acgggccgcc gcccaccccg agcccagacc gcgacgagcg gggggccctc gggtggggcg | 180 |
| cggagacgga ggagggcggg gacgaccccg accacgaccc cgaccacccc cacgacctcg | 240 |
| acgacgcccg gcgggacggg agggcccccg cggcggcac cgacgccggc gaggacgccg | 300 |
| gggacgccgt ctcgccgcga cagctggctc tgctggcctc catggtagag gaggccgtcc | 360 |
| ggacgatccc gacgcccgac cccgcggcct cgccgcccg accccgcc tttcgagccg | 420 |
| acgacgatga cggggacgag tacgacgacg cagccgacgc cgccggcgac cgggccccgg | 480 |
| cccggggccg cgaacgggag gccccgctac gcggcgcgta tccggacccc acggaccgcc | 540 |
| tgtcgccgcg cccgccggcc cagccgccgc ggagacgtcg tcacggccgg tggcggccat | 600 |
| cggcgtcatc gacctcgtcg gactccgggt cctcgtcctc gtcgtccgca tcctcttcgt | 660 |
| cctcgtcgtc cgacgaggac gaggacgacg acggcaacga cgcggccgac cacgcacgcg | 720 |
| aggcgcgggc cgtcgggcgg ggtccgtcga gcgcggcgcc ggcagccccc gggcggacgc | 780 |
| cgcccccgcc cgggccaccc cctctccg aggccgcgcc caagccccgg gcggcggcga | 840 |
| ggaccccgc ggcctccgcg ggcgcatcg agcgccgccg ggcccgcgcg cggtggccg | 900 |
| gccgcgacgc cacgggccgc ttcacggccg ggcagccccg gcgggtcgag ctggacgccg | 960 |
| acgcgacctc cggcgccttc tacgcgcgct atcgcgacgg gtacgtcagc ggggagccgt | 1020 |
| ggcccggcgc cgggcccccg cccccgggc gggtgctgta cggcggcctg ggcgacagcc | 1080 |
| gccccggcct ctgggggcg cccgaggcgg aggaggcgcg acgccggttc gaggcctcgg | 1140 |
| gcgccccggc ggccgtgtgg gcgcccgagc tgggcgacgc cgcgcagcag tacgccctga | 1200 |
| tcacgcggct gctgtacacc ccggacgcgg aggccatggg gtggctccag aacccgcgcg | 1260 |
| tggtccccgg ggacgtggcg ctggaccagg cctgcttccg gatctcgggc gccgcgcgca | 1320 |
| acagcagctc cttcatcacc ggcagcgtgg cgcgggccgt gccccacctg ggctacgcca | 1380 |
| tggcggccgg ccgcttcggc tggggcctgg cgcacgcggc ggccgccgtg ccatgagcc | 1440 |
| gccgatacga ccgcgcgcag aagggcttcc tgctgaccag cctgcgccgc gcctacgcgc | 1500 |
| ccctgttggc gcgcgagaac gcggcgctga cggggccgc ggggagcccc ggcgccggcg | 1560 |
| cagatgacga gggggtcgcc gccgtcgccg ccgccgcacc gggcgagcgc gcggtgcccg | 1620 |
| ccgggtacgg cgccgcgggg atcctcgccg ccctggggcg gctgtccgcc gcgcccgcct | 1680 |
| cccccgcggg gggcgacgac cccgacgccg ccgccacgc cgacgccgac gacgacgccg | 1740 |

-continued

```
ggcgccgcgc ccaggccggc cgcgtggccg tcgagtgcct ggccgcctgc cgcgggatcc      1800
tggaggcgct ggccgagggc ttcgacggcg acctggcggc cgtcccgggg ctggccgggg      1860
cccggcccgc cagcccccg cggccggagg gacccgcggg ccccgcttcc ccgccgccgc       1920
cgcacgccga cgcgccccgc ctgcgcgcgt ggctgcgcga gctgcggttc gtgcgcgacg      1980
cgctggtgct catgcgcctg cgcggggacc tgcgcgtggc cggcggcagc gaggccgccg      2040
tggccgccgt gcgcgccgtg agcctggtcg ccggggccct gggccccgcg ctgccgcggg      2100
acccgcgcct gccgagctcc gcggccgccg ccgccgcgga cctgctgttt gacaaccaga      2160
gcctgcgccc cctgctggcg gcggcggcca gcgcaccgga cgccgccgac gcgctggcgg      2220
ccgccgccgc ctccgccgcg ccgcgggagg ggcgcaagcg caagagtccc ggcccggccc      2280
ggccgcccgg aggcggcggc ccgcgacccc cgaagacgaa gaagagcggc gcggacgccc      2340
ccggctcgga cgcccgcgcc cccctccccg cgcccgcgcc cccctccacg ccccgggc        2400 ccgagcccgc ccccgcccag cccgcggcgc cccgggccgc cgcggcgcag gcccgcccgc      2460
gccccgtggc cgtgtcgcgc cggcccgccg agggccccga ccccctgggc ggctggcggc      2520
ggcagccccc ggggcccagc cacacggcgg cgcccgcggc cgccgccctg gaggcctact      2580
gctccccgcg cgccgtggcc gagctcacgg accacccgct gttcccgtc ccctggcgac       2640 cggccctcat gtttgacccg cgggccctgg cctcgatcgc cgcgcggtgc gccgggcccg      2700 ccccgccgc ccaggccgcg tgcggcggcg gcgacgacga cgataacccc caccccacg        2760 gggccgccgg gggccgcctc tttggccccc tgcgcgcctc gggcccgctg cgccgcatgg      2820
cggcctggat gcgccagatc cccgaccccg aggacgtgcg cgtggtggtg ctgtactcgc      2880
cgctgccggg cgaggacctg gccggcgcg gggcctcggg ggggccgccg gagtggtccg       2940
ccgagcgcgg cgggctgtcc tgcctgctgg cggccctggc caaccggctg tgcgggccgg      3000
acacggccgc ctgggcgggc aattggaccg gcgcccccga cgtgtcggcg ctgggcgcac      3060
agggcgtgct gctgctgtcc acgcgggacc tggccttcgc cggggccgtg gagtttctgg      3120
ggctgctcgc cagcgccggc gaccggcggc tcatcgtggt caacaccgtg cgcgcctgcg      3180
actgccccgc cgacgggccc gcggtgtcgc ggcagcacgc ctacctggcg tgcgagctgc      3240
tgcccgccgt gcagtgcgcc gtgcgctggc cggcggcgcg ggacctgcgc cgcacggtgc      3300
tggcctcggg ccgcgtgttc ggcccggggg tcttcgcgcg cgtggaggcc gcgcacgcgc      3360
gcctgtaccc cgacgcgccg ccgctgcgcc tgtgccgcgg cggcaacgtg cgctaccgcg      3420
tgcgcacgcg cttcggcccg gacacgccgg tgcccatgtc cccgcgcgag taccgccggg      3480
ccgtgctgcc ggcgctggac ggccgggcgg cggcctcggg gaccaccgac gccatggcgc      3540
ccggcgcgcc ggacttctgc gaggaggagg cccactcgca cgccgcctgc gcgcgctggg      3600
gcctgggcgc gccgctgcgg cccgtgtacg tggcgctggg gcgcgaggcg gtgcgcgccg      3660
gcccggcccg gtggcgcggg ccgcggaggg acttttgcgc ccgcgccctg ctggagcccg      3720
acgacgacgc ccccccgctg gtgctgcgcg gcgacgacga cggcccgggg gccctgccgc      3780
cggcgccgcc cgggattcgc tgggcctcgg ccacggccg cagcggcacc gtgctggcgg      3840 cggcggggc cgtggaggtg ctgggggcgg aggcgggctt ggccacgccc ccgcggcggg      3900
aagttgtgga ctgggaaggc gcctgggacg aagacgacgg cggcgcgttc gaggggacg       3960 gggtgctgta aaggcctaaa taataatttt ttat                                 3994
```

<210> SEQ ID NO 14
<211> LENGTH: 1636
<212> TYPE: DNA

-continued

```
<213> ORGANISM: Artificial Sequence
<220> FEATURE:
<223> OTHER INFORMATION: expression cassette

<400> SEQUENCE: 14
aaaaattgaa attttatttt ttttttttgg aatataaata aggaattcct gcaggctagc      60
cccgggaagc ttccatggcg actgacattg atatgctaat tgacctcggc ctggacctct     120
ccgacagcga tctggacgag gacccccccg agccggcgga gagccgccgc gacgacctgg     180
aatcggacag cagcggggag tgttcctcgt cggacgagga catggaagac ccccacggag     240
aggacggacc ggagccgata ctcgacgccg ctcgcccggc ggtccgcccg tctcgtccag     300
aagaccccgg cgtacccagc acccagacgc ctcgtccgac ggagcggcag ggccccaacg     360
atcctcaacc agcgccccac agtgtgtggt cgcgcctcgg ggcccggcga ccgtcttgct     420
cccccgagca gcacggggc aaggtggccc gcctccaacc cccaccgacc aaagcccagc      480
ctgcccgcgg cggacgccgt gggcgtcgca ggggtcgggg tcgcggtggt cccggggctg     540
ccgatggttt gtcggacccc cgccggcgtg cccccagaac caatcgcaac cctgggggac     600
cccgccccgg ggcggggtgg acggacggcc ccggcgcccc ccatggcgag gcgtggcgcg     660
gcagtgagca gcccgaccca cccggaggcc agcggacacg gggcgtgcgc caagcacccc     720
ccccgctaat gacgctggcg attgccccc cgcccgcgga ccccgcgcc ccggcccgg       780
agcgaaaggc gcccgccgcc gacaccatcg acgccaccac gcggttggtc ctgcgctcca     840
tctccgagcg cgcggcggtc gaccgcatca gcgagagctt tggccgcagc gcacaggtca     900
tgcacgaccc ctttgggggg cagccgtttc ccgccgcgaa tagcccctgg gccccggtgc     960
tggcgggcca aggagggccc tttgacgccg agaccagacg ggtctcctgg gaaaccttgg    1020
tcgcccacgg cccgagcctc tatcgcactt ttgccggcaa tcctcgggcc gcatcgaccg    1080
ccaaggccat gcgcgactgc gtgctgcgcc aagaaaattt catcgaggcg ctggcctccg    1140
ccgacgagac gctggcgtgg tgcaagatgt gcatccacca caacctgccg ctgcgccccc    1200
aggaccccat tatcgggacg accgcggctg tgctggataa cctcgccacg cgcctgcggc    1260
cctttctcca gtgctacctg aaggcgcgag gcctgtgcgg cctggacgaa ctgtgttcgc    1320
ggcggcgtct ggcggacatt aaggacattg catccttcgt gtttgtcatt ctggccaggc    1380
tcgccaaccg cgtcgagcgt ggcgtcgcgg agatcgacta cgcgacccctt ggtgtcgggg   1440
tcggagagaa gatgcatttc tacctccccg gggcctgcat ggcgggcctg atcgaaatcc    1500
tagacacgca ccgccaggag tgttcgagtc gtgtctgcga gttgacggcc agtcacatcg    1560
tcgccccccc gtacgtgcac ggcaaatatt tttattgcaa ctccctgttt tagaggccta    1620
aataaataat ttttat                                                    1636

<210> SEQ ID NO 15
<211> LENGTH: 165
<212> TYPE: DNA
<213> ORGANISM: Artificial Sequence
<220> FEATURE:
<223> OTHER INFORMATION: expression cassette

<400> SEQUENCE: 15
gtgagctcac attcaaagag tcttaagata taactcgaga aaaattgaaa ttttattttt     60
ttttttgga atataaataa ggaattcctg caggctagcc ccgggaagct tccatggagg     120
cctaaataaa aattttttat ggatccggag agctcgggta tctag                    165

<210> SEQ ID NO 16
```

-continued

```
<211> LENGTH: 10
<212> TYPE: PRT
<213> ORGANISM: Vaccinia virus

<400> SEQUENCE: 16

Val Ser Ser His Ser Lys Ser Leu Lys Ile
1               5                   10
```

METHODS AND COMPOSITIONS FOR THE PRODUCTION OF RECOMBINANT VIRUS VECTORS

GOVERNMENT INTERESTS

This invention was made with government support under Grant No. R01HL080789 awarded by the National Institute of Health. The United States government has certain rights in this invention.

TECHNICAL FIELD

The technical field generally relates to virology and molecular biology and, in particular, to compositions and methods for the production of recombinant viral vectors.

BACKGROUND

A recombinant viral vector carrying a foreign DNA insert may be used to deliver genes to cells, where the gene may be expressed to permit production of polypeptides or polynucleotides (e.g., miRNA, RNAi, antisense RNAs) for the treatment or amelioration of diseases or genetic defects in humans or non-human mammals. The foreign DNA insert may also be used for DNA recombination and repair of genes, and no expression would necessary under such circumstances.

Recombinant viral vectors that are commonly used in gene delivery applications are typically defective in one or more genes that are required for viral reproduction, so that the recombinant viral vectors cannot reproduce themselves in patients receiving the treatment. During the production of a recombinant virus, the defective gene or genes are provided in trans, i.e., from a DNA sequence that is physically separated from the recombinant viral genome, so as to permit replication and encapsidation of the recombinant virus. However, since the DNA sequence and the recombinant viral genome are both present in the nucleus of the host cell, recombination events between the DNA sequence and the recombinant viral genome may result in replication-competent viruses that are undesirable for treatment purpose.

Therefore, there still exists a need for methods that are capable of producing recombinant viral vectors that are not contaminated with replication competent viruses and that can be easily scaled-up for industrial production.

SUMMARY OF THE INVENTION

A method for eliminating or minimizing the formation of replication-competent virus during the production of a replication-deficient recombinant virus vector is disclosed. The replication-deficient recombinant virus vector has a recombinant virus genome with one or more defective viral genes. The method includes infecting a host cell with a carrier virus having a carrier virus genome encoding one or more trans factors or variants thereof, incubating the infected host cell for a desired period of time, and isolating the replication-deficient recombinant virus vector. The carrier virus is a cytoplasmic virus that retains the carrier virus genome in the cytoplasm of the host cell. The one or more trans factors compensate one or more functions of the one or more defective genes in the recombinant virus genome. The one or more trans factors include a structure protein of the replication-deficient recombinant virus. The host cell contains the recombinant viral genome and retains the recombinant viral genome in a nucleus of the host cell.

Also disclosed is a method for producing a replication-deficient recombinant virus vector having a recombinant virus genome with one or more defective viral genes. The method includes infecting a host cell with a carrier virus having a carrier virus genome encoding one or more trans factors or variants thereof, incubating the infected host cell for a desired period of time; and isolating said replication-deficient recombinant virus vector. The carrier virus is a cytoplasmic virus that retains the carrier virus genome in the cytoplasm of the host cell and wherein the one or more trans factors compensate one or more functions of the one or more defective genes in the recombinant virus genome. The host cell contains the recombinant viral genome and retains the recombinant viral genome in a nucleus of the host cell. The replication-deficient recombinant virus vector is selected from the group consisting of recombinant virus vectors from the Adenoviridae family, the Herpesviridae family, the Hepadnaviridae family, and recombinant recombinant parvovirus vectors.

Also disclosed is a method for producing a replication-deficient recombinant AAV vector having a recombinant virus genome that is defective in producing capsid proteins. The method includes infecting a host cell with one or more carrier viruses, incubating the infected host cell for a desired period of time, and isolating the replication-deficient recombinant virus vector. The carrier viruses are cytoplasmic viruses that encode two or more AAV capsid proteins and express the two or more capsid proteins in the cytoplasm of the host cell in a ratio suitable for the production of the replication-deficient AAV vector. The host cell contains the recombinant AAV genome and retains the recombinant AAV genome in a nucleus of the host cell.

Also disclosed is a carrier virus. The carrier virus comprises a capsid and a carrier virus genome that comprises a nucleic acid sequence from a cytoplasmic virus and a nucleotide sequence that encodes two or more AAV structure proteins or variants thereof. The capsid and the nucleic acid sequence from a cytoplasmic virus allow the carrier virus genome to remain in the cytoplasm after entering a host cell. The carrier virus genome expresses the two or more AAV structure proteins or variants thereof in the cytoplasm at a ratio suitable for the production of a recombinant AAV vector that is defective in the two or more AAV structure proteins.

DETAILED DESCRIPTION

Figure 1:
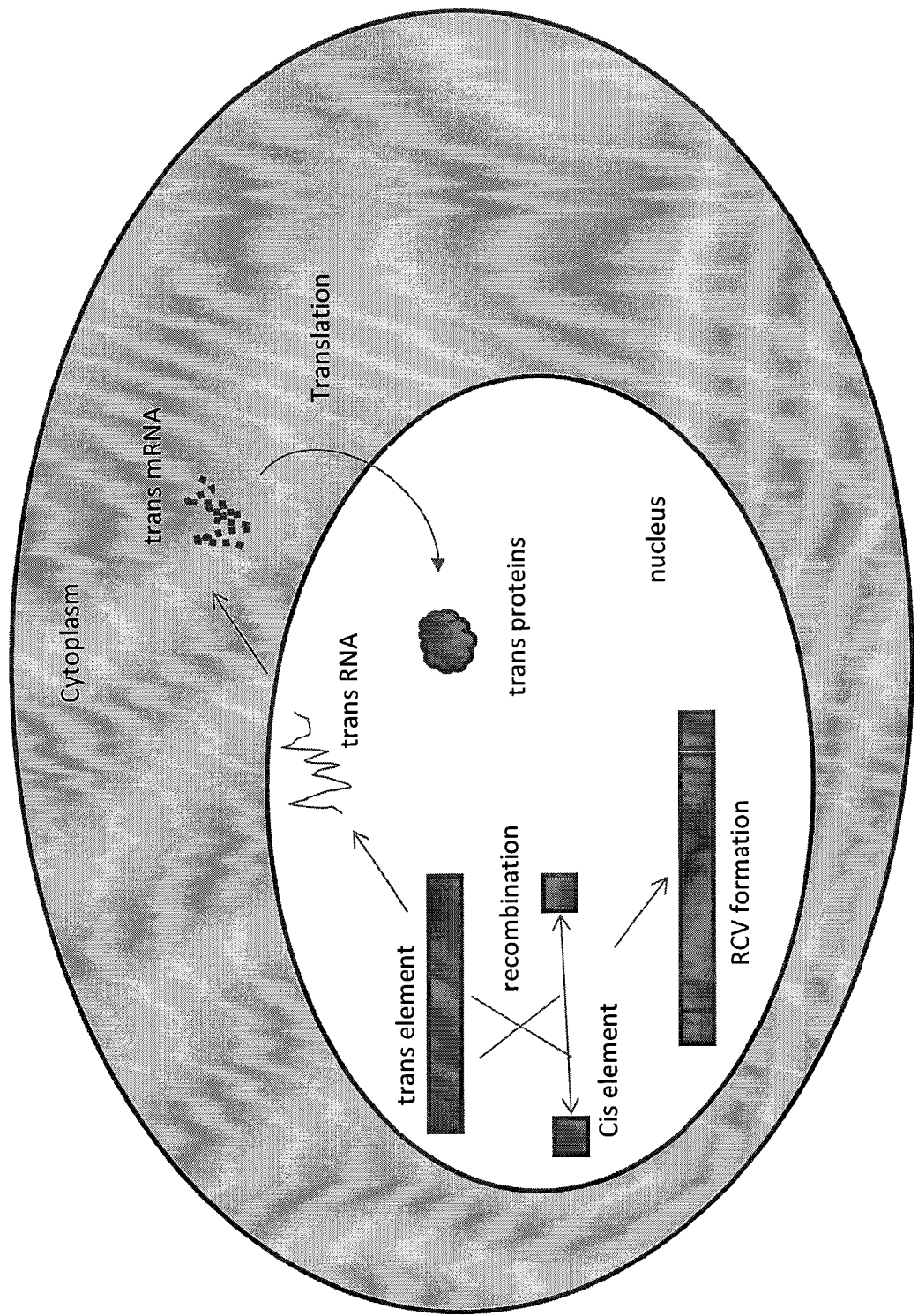
FIG. 1 is a diagram showing the prior art method for producing recombinant viral vectors.

Unless otherwise defined, all technical and scientific terms used herein have the meaning as commonly understood by one of ordinary skill in the art to which this invention belongs. All the references cited hereinafter are incorporated by reference in their entirety. The practice of the present invention employs, unless otherwise indicated, conventional techniques of chemistry, molecular biology, microbiology, recombinant DNA, genetics, virology and immunology. See, e.g., Sambrook et al., 2000. Molecular Cloning: A Laboratory Manual, Harlow et al.

A "recombinant viral vector" or a "recombinant virus" refers to a virus produced by recombinant DNA technology. A recombinant virus may be defective in one or more genes that are required for viral reproduction and is, therefore, replication-deficient (i.e., the recombinant virus cannot reproduce itself in a patient receiving the recombinant virus.

A "recombinant viral genome" or "cis element" refers to all the genetic information contained in a recombinant virus. A recombinant viral genome may contain all or a part of a viral genome, wherein the viral genome may be wild-type or may contain point mutations, insertions or deletions. A recombinant viral genome may optionally comprises a transgene operably linked to expression control sequences. The transgene may be flanked by flanking elements. The recombinant viral genome of the invention may be integrated into the host chromosome, or transfected into a host nucleus by physical or chemical methods, or delivered into the host nucleus using a virus vector targeting into the nucleus of the host cells, and is ultimately packaged into a recombinant viral vector.

A "flanking element" or "flanking nucleic acid" is a nucleic acid sequence generally derived from a mammalian virus which, when located in positions flanking a transgene, permits the packaging of the transgene into a recombinant viral vectors. Flanking elements may be the naturally-occurring flanking elements from a mammalian virus which permit the packaging of the recombinant viral vectors, or may be artificial nucleic acid elements, e.g. mutated sequences of flanking elements, that have the same or similar packaging function. Flanking elements include, without limitation, the inverted terminal repeats (ITRs) of adeno-associated virus (AAV) or adenovirus (Ad, the long terminal repeats (LTRs) of retrovirus, the "a" or packaging sequence of herpes simplex virus (HSV), as well as any other sequences that are required for packaging from other viruses known in the art.

A "transgene" is a nucleic acid sequence that is to be delivered or transferred to a mammalian cell. A transgene may encode a protein, peptide or polypeptide that is useful as a marker, reporter or therapeutic molecule. A transgene may also encode a protein, polypeptide or peptide that is useful for protein production, diagnostic assays or for any transient or stable gene transfer in vitro or in vivo. Alternatively, a transgene may encode a functional polynucleotide, such as miRNA, RNAi, antisense RNAs, ribozyme or other regulatory nucleic acids. Transgenes also include DNA sequences that are used to induce DNA recombination and gene repair.

"Expression control sequences" or "regulatory sequences" are nucleic acid sequences that regulate the expression of a gene by being operably linked to the gene of interest. Examples of regulatory sequences include, but are not limited to, appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. A regulatory sequence may act in cis or trans configuration, or at a distance to control a gene of interest.

A nucleic acid sequence is "operably linked" to another nucleic acid sequence when the former is placed into a functional relationship with the latter. For example, a DNA for a presequence or secretory leader peptide is operably linked to DNA for a polypeptide if it is expressed as a preprotein that participates in the secretion of the hepolypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accordance with conventional practice.

As used herein, the term "expression cassette" refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals The term "trans factor" refers to a viral protein that is required for the production of a recombinant virus and is not functionally expressed from the genome of the recombinant virus. A recombinant virus vector may need the help from one or more trans factors to replicate in a host cell. A trans factor can be a wide-type viral protein or a variant of a viral protein. Proteins that can be used as trans factors for the production of recombinant AAV include Rep78, Rep68, Rep 52, rep 40, VP1, VP2 and VP3. Proteins that can be used as trans factors for the production of recombinant parvovirus vectors include NS1, NS2, VP1-3. Proteins that can be used as trans factors for the production of recombinant adenovirus include various adenovirus early gene products and adenovirus later gene products, such as E1a, E1b, E2a, E3, E4, and L1-L5. Proteins that can be used as trans factors for the production of recombinant herpes virus include herpes virus early gene products and herpes virus later gene products (e.g., ICP4, ICP27 etc.).

The term "trans factor nucleic acid sequence" refers to a nucleic acid sequence that encodes a trans factor.

The term "trans cassette" refers to an expression cassette that encodes and expresses one or more trans factors.

The term "trans element" refers to a polynucleotide that comprises a trans factor nucleic acid sequence. A trans element may comprises a trans cassette.

The term "carrier virus" refers to a recombinant cytoplasmic virus that carries a trans element in its genome. Examples of carrier viruses include vaccinia carrier virus carrying the herpes ICP4 and/or ICP27 genes for the production of recombinant herpes viral vectors; vaccinia carries virus carrying the AAV vp1 and vp2 genes for the production of recombinant AAV; and VSV carrier viruses carrying the adenovirus E1a and E1b genes for the production of recombinant adenovirus vectors.

The term "cytoplasmic virus" refers to a virus whose nucleic acids predominantly reside in the cytoplasm of the host cells during the infection. Examples of cytoplasmic viruses include, but are not limited to, members of the Poxviridae family, such as variola virus, vaccinia virus, cowpox virus, monkeypox virus, smallpox, pseudocowpox, bovine papular stomatitis virus, tanapox virus, yaba monkey tumor virus molluscum contagiosum virus (MCV), and members of RNA viruses family which does not use a DNA intermediate, such as vesicular stomatitis virus (VSV), Semliki forest virus and Sindbis virus vectors etc.

A "nucleus targeting vector" is a plasmid or viral vector that contains a nuclear anchoring element and is capable of introducing the vector DNA into the nuclei of a cell. Any retrovirus or DNA virus that replicates in the nucleus can be used as nucleus targeting vector. When a viral vector is used as a nucleus targeting vector, it may be referred to as a "virus-based nucleus targeting vector." For example, when a recombinant adenovirus vector carrying a recombinant AAV genome is used as a nucleus targeting vector to introduce the recombinant AAV genome into the nucleus of a host cell, the recombinant adenovirus vector may be referred to as an "adenovirus-based nucleus targeting vector."

The term "nuclear anchoring element" refers to a nuclei acid sequence of a nucleic acid molecule that is retained in a nucleus of a cell, especially in a nucleus of a human cell. This nucleic acid molecule, being a vector and having the nuclear anchoring element, anchors to a nuclear matrix of the nucleus. Examples of a nuclear anchoring element includes, but not limited to, an EBV gene encoding an EBV nuclear protein (e.g., nuclear antigen-1 (EBNA-1)) and an EBV origin (i.e., an EBV replicon, oriP); a papovavirus origin of replication and a papovavirus large T antigen; or a polyomavirus (Py) origin (PyOri) and large T (LT) antigen gene (PyLT) (See e.g., Heffernan and Dennis, 1991, Nucleic Acids Res. 19:85-92).

A "viral regulatory protein" refers to a viral protein that regulates transcription of a viral gene or a host gene.

A "viral structure protein," as used hereinafter, refers to a viral protein that does not regulate transcription. Viral structure proteins are coded by viral structural genes and include nucleocapsid core proteins (such as gag proteins), enzymes (such as pol proteins), and membrane components (such as env proteins). Transcription of viral structural genes is regulated by viral regulatory proteins (such as rep proteins).

A "variant" of a polypeptide is a polypeptide that differs from a native polypeptide in one or more substitutions, deletions, additions and/or insertions, such that the biological activity of the polypeptide is not substantially diminished. In other words, the variant of a protein has similar biological activity or activities as the native protein. In certain embodiments, the biological activity or activities of the variant may be enhanced or unchanged, relative to the native protein, or may be diminished by less than 50%, and preferably less than 20%, relative to the native protein. Preferred variants include those variants in which a small portion (e.g., 1-30 amino acids, preferably 5-15 amino acids) has been removed from the N- and/or C-terminal of the mature protein.

Preferably, a variant polypeptide contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gin, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide. Polypeptide variants preferably exhibit at least about 70%, more preferably at least about 90% and most preferably at least about 95% homology to the original polypeptide.

A polypeptide variant also include a polypeptides that is modified from the original polypeptides by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination.

Figure 2:
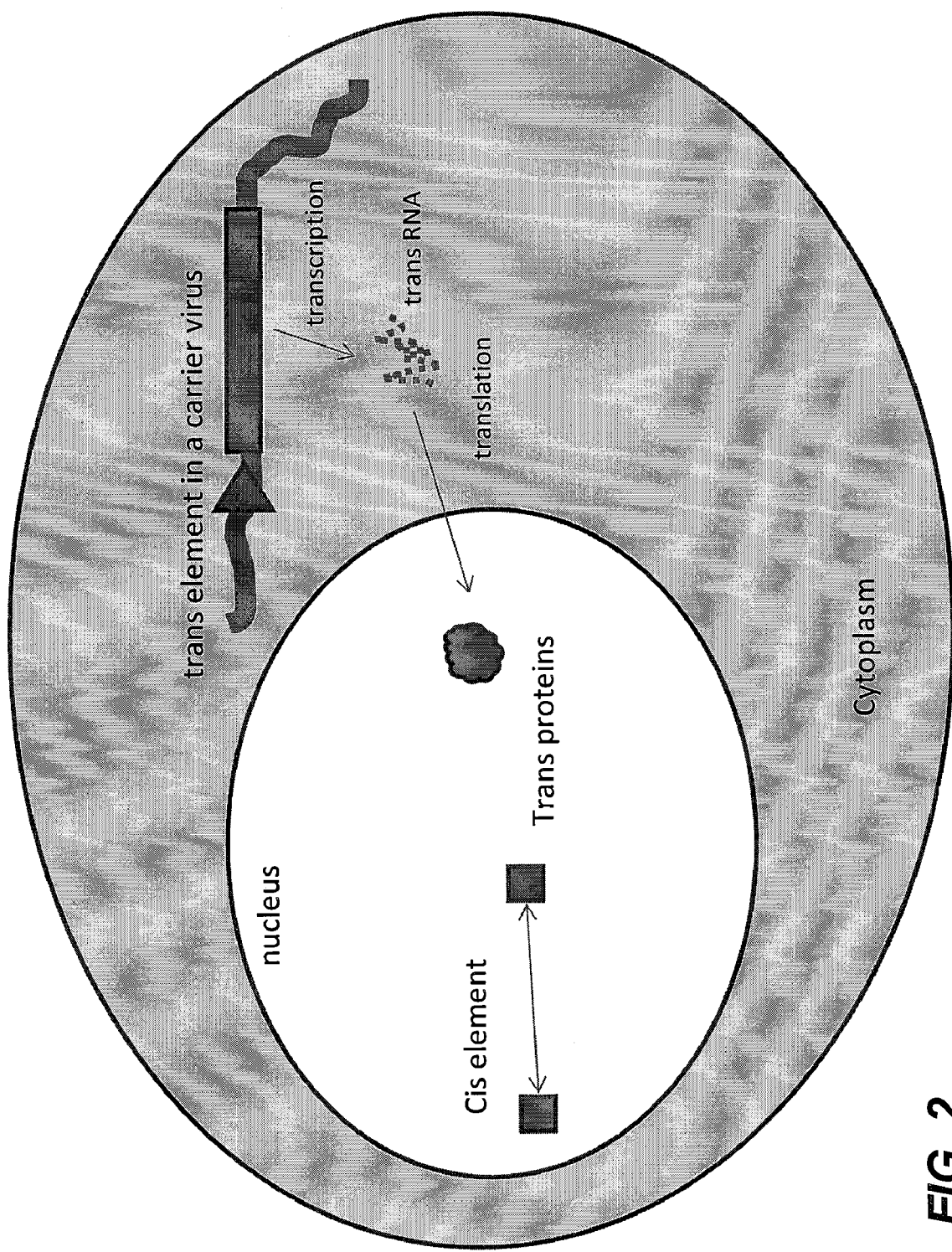
FIG. 2 is a diagram showing a method for producing replication-competent virus (RCV) free recombinant virus vectors by sequestering the trans elements and cis elements in different cellular compartments

The present invention exploits the properties of cytoplasm born viruses for the creation of novel carrier viruses. The carrier viruses can be used for the manufacture of replication-deficient recombinant viral vectors that are free from replication-competent virus (RCV) particles. FIG. 1 shows a prior art system in which both the trans element and the cis element are located in the nucleus of the host and thus allowing the formation of RCV genome by recombination between the trans and cis elements. FIG. 2 shows the concept of producing RCV-free recombinant viral vectors by sequestering the trans element and cis element in different cellular compartments. The trans element, which encodes one or more trans factors, resides in the cytoplasm. The cis element, which carries the replication/packaging signals and the transgene, resides in the nucleus of the host cells. The trans factors are transcribed and translated in the cytoplasm and then transported into the nucleus because there are generally nuclear-localization signals in the trans factors. Since the trans elements and the cis elements never meet each other in the same cellular compartment, the possibility of recombination between the two elements, and hence the generation of RCV, is minimized or eliminated.

One aspect of the present invention relates to a method for eliminating or minimizing the formation of replication-competent virus during the production of a replication-deficient recombinant virus having a recombinant viral genome that is defective in one or more viral genes required for viral DNA replication or viral particle production. The method includes the steps of infecting a host cell with at least one or more carrier virus carrying the coding sequence of one or more trans factors or variants thereof that compensate the function of at least one defective gene in the recombinant viral genome, incubating the infected host cell for a desired period of time, and isolating the recombinant virus. The carrier virus is a cytoplasmic virus that retains its viral genome in the cytoplasm of the host cell and expresses the one or more trans factors in the cytoplasm of the host cell. The host cell contains the recombinant viral genome and retains the recombinant viral genome in the nucleus of the host cell.

In certain embodiments, the one or more trans factors include a structure protein of the recombinant viral vector. In other embodiments, the one or more trans factors include only the structure proteins of the recombinant viral vector. In yet other embodiments, the one or more trans factors include both the structure proteins and non-structural proteins of the recombinant viral vector.

The term "replication-competent virus" as used hereinafter, refers to a viral particle that is derived from a replication-deficient recombinant virus and is capable of reproducing infectious virus particles in a host cell in which the replication-deficient recombinant virus cannot reproduce itself. A replication-competent virus typically arises from the homologous or non homologous recombination between the genome of the replication-deficient recombinant virus (e.g., the cis element) and the trans factors genes (e.g., the trans element). The cis element acquires partial or full trans factor functions through the recombination event and gains the ability to reproduce infectious virus particles in the host cell. Replication-competent viruses are often produced in the conventional production system because the cis elements and trans elements are both abundantly present in the nucleus of the host cells. The method of the present invention minimizes or eliminates the likelihood of recombination events between the cis and trans cassettes by retaining the cis and trans cassettes in separate cellular departments.

The Carrier Virus

The carrier virus can be any cytoplasmic virus. A cytoplasmic virus retains its genome in the cytoplasm and can be distinguished from viruses that regularly replicate in the nucleus of the host cells. Cytoplasmic carrier virus with trans factor gene(s) incorporated into its genome inherits from the parental wild type virus the property to remain in the cytoplasm after entering a host cell. The carrier virus genome may contain native sequences from a wild-type cytoplamic virus or a modified sequence from a wild-type cytoplamic virus, so long as the genome or the viral capsids retain the function that allows the carrier virus genome to remain in the cytoplasm after entering a host cell. The carrier virus may carry deletions in multiple regions to have more spaces for carrying trans factors. Exogenous genes from different virus may be incorporated into the carrier virus to control the infectivity and tissue tropism of the carrier virus. Chemical conjugation of ligands or non-genetic engineering methods such as formulation may also be used to improve the efficiency of the carrier virus.

In a preferred embodiment, the carrier virus is derived from vaccinia virus. In certain embodiments, multiple vaccinia carrier viruses are used for the production of the recombinant viral vectors and each vaccinia carrier virus carries a trans factor gene. The sequences encoding the trans factors were inserted into the vaccinia virus genome under the control of vaccinia virus promoters or synthetic promoters. Alternatively, the trans factor gene can be controlled by a T7 promoter while T7 RNA polymerase is expressed from a vaccinia virus or the host cells. In other embodiments, one vaccinia carrier virus carries two or more trans factor genes. In a preferred embodiment, a single vaccinia carrier virus carrying all necessary trans factors is used for the production of the recombination viral vectors.

The trans factors that are required for the production of a recombinant viral vector differ depending upon the type of recombinant viral vector and the host cell. The required trans factors for commonly used recombinant viral vectors are known in the art. For example, recombinant AAV vectors typically require the functions of rep and cap for replication and encapsidation, recombinant adenovirus vectors typically require all or part of the functions encoded by E1, E2, E4, L1-L5, pIX and IVa2 genes, alone or in combination, and recombinant herpes virus vectors typically require the functions encoded a large number of genes including UL6, UL18, UL35, UL38 and the major capsid protein UL19, ICP0, RS1 (ICP4) and UL54 (ICP27). In general, the host mammalian cell and the carrier virus together must contribute the necessary replication and encapsidation functions for the particular recombinant viral vectors in order to obtain infectious recombinant viral vectors from the mammalian host cells.

The carrier virus may further include a regulatory sequence that regulates the expression of the trans factor nucleic acid sequence or other nucleic acid sequences in the carrier virus. Since the carrier virus resides in the cytoplasm, the regulatory elements for controlling the expression of the trans factor nucleic acid sequence need to be functional in cytoplasm. For example, when poxviruses are used as carrier viruses, cytoplasmic promoters will have to be used to control gene expression. In addition, RNA splicing is lacking for cytoplasmic viruses, different templates will have to be used for gene expression if the proteins are translated from the spliced RNA templates.

The regulatory sequence may comprise a constitutive promoter and/or enhancer. Examples of such promoter/enhancers include, but are not limited to, vaccinia virus p7.5 promoter, vaccinia virus PL11 promoter, I1L promoter (Schmitt and Stunnenberg, 1988, J. Virol. 62, 1889-1897), A10L promoter (Wittek et al., 1984, J. Virol. 49, 371-378), J3R (Senkevich et al., 1997, Virology 233, 19-42), E4L promoter (Ahn et al., 1990, Mol. Cell. Biol. 10, 5433-5441), F17R promoter (Wittek et al. 1984, Nucl. Acids Res. 12, 4835-4848), A1L promoter (Keck et al., 1990, Cell 61, 801-809), and cowpox A-type inclusion (ATI) late promoter.

The regulatory sequence may also comprise an inducible promoter and/or enhancer. Examples of cytoplasmic inducible promoters include, but are not limited to, the hybrid vaccinia/T7 system, in which a bacteriophage T7 RNA polymerase is used to drive transcription from a T7 promoter (Elroy-Stein et al., 1989, Proc. Nat. Acad. Sci. U.S.A. 86, 6126-6130, and Ward et al., 1995, Proc. Nat. Acad. Sci. U.S.A. 92, 6773-6777). Since T7 RNA polymerase can be expressed the host nucleus, many conventional inducible promoters can be used as Tet-on and Tet-off system, MMTV inducible promoter and others.

In certain embodiments, each protein or polypeptide required for recombinant viral vector production is encoded by a nucleic acid whose expression is regulated by its own cytoplasmic promoter and transcription stop signal, as well as optional sequences such as enhancers. In another embodiment, a trans factor nucleic acid sequence is transcribed to a single transcript that encodes more than one protein or polypeptide required for recombinant viral vector function. In this case, an internal ribosome entry site (IRES) may be placed between the coding sequences of each of the individual proteins or polypeptide to permit subsequent translation of the polycistronic mRNA.

In one embodiment, the carrier vector comprises a trans factor nucleic acid sequence for the production of recombinant AAV. The carrier viruses can be a single virus, a mixture of several viruses of the same type (e.g., several vaccinia carrier viruses each carrying a different trans factors), or a mixture of different types of viruses (e.g., a vaccinia virus carrying a VP1 and a VSV carrying Rep78). In a preferred embodiment, the carrier viruses are vaccinia viruses. In a more preferred embodiment, a single vacinnia carrier virus carrying the AAV rep78, rep 52, rep68, rep 40, vp1, vp2 and vp3 genes is used for the production of recombinant AAV. In another preferred embodiment, a single vacinnia carrier virus carrying the AAV rep78, rep 52, vp1, vp2 and vp3 genes is used for the production of recombinant AAV. In another preferred embodiment, a single vacinnia carrier virus carrying the AAV rep68, rep 52, vp1, vp2 and vp3 genes is used for the production of recombinant AAV. In yet another preferred embodiment, a single vacinnia carrier virus carrying the AAV rep78, rep 52, rep68, rep 40, vp1 and vp2 genes is used for the production of recombinant AAV.

In wild type AAV virus, three capsid genes vp1, vp2 and vp3 overlap each other. A single P40 promoter allows all three capsid proteins to be expressed at a ratio of 1:1:10, which complement with rAAV production. For the production of recombinant AAV vectors, desired ratio of VP1:VP2:VP3 is in the range of about 1:1:1 to about 1:1:100, preferably in the range of about 1:1:2 to about 1:1:50, more preferably in the range of about 1:1:5 to about 1:1:20. Although the desired ratio of VP1:VP2 is 1:1, the ratio range of VP1:VP2 could vary from 1:50 to 50:1. In addition, optimal ratio of Rep78 and Rep52 can be controlled as well. Desired Rep78: Rep52 ratio is in the range of 2:1 to 1:200, preferably in the range of 1:1 to 1:50.

Applicant has found surprisingly that vp2 gene with acg as start codon in a vaccinia carrier virus under the control of p7.5 promoter was able to express a desired ratio of VP2 and VP3 for the production of recombinant AAV. Similarly, vp1 gene with native ATG starting codon in a vaccinia carrier virus was able to express a VP1 and VP3 for the production of recombinant AAV. A mutation of VP1 ATG starting codon to a weak initiation codon like ACG will also help achieve correct ratio of VP1: VP2:VP3 for AAV production. Change of VP2 starting codon to ATG will have an effect on VP2 and VP3 expression as well. Vaccinia carrier virus with both vp1 gene and vp2 gene easily achieved the optimal ratio of VP1, VP2 and VP3 for rAAV production. The desired VP1:VP2:VP3 and/or Rep78: Rep52 ratio can also be obtained by infecting the host cell with multiple viruses at different MOIs (e.g., a first vaccinia virus carrying the vp1 gene at MOI of 1 and a second vaccinia virus carrying the vp2 gene at another MOI).

One advantage of using vaccinia carrier virus carrying one or more of AAV rep78, rep 52, rep68, rep 40, vp1, vp2 and vp3 genes, is that the carrier viruses can be stably maintained and produced. When homologous sequences like vp1 and vp2 are incorporated into a single carrier virus, it is optimal to place them further away in the carrier virus to increase the carrier virus stability. For example, vp1 and rep78 are placed at tk gene locus and vp2 and rep52 are placed at the vp37 locus.

In another preferred embodiment, one vacinnia carrier virus carrying the AAV rep78 and vp1 and one vacinnia carrier virus carrying rep52 and vp2 are used for the production of recombinant AAV. Under this condition, there are no homologous sequences (i.e rep78 vs rep52 or vp1 vs vp2) in any carrier virus. Carrier virus tends to be more stable when there are no homologous DAN sequences. Permutations of rep and capsid genes can be arranged differently. In yet another preferred embodiment, one vacinnia carrier virus carrying the AAV rep78 and vp2 one vacinnia carrier virus carrying rep52 and vp1 are used for the production of recombinant AAV.

AAV has more than 100 serotypes and many modified capsids and the carrier virus can be easily modified to accommodate the production of each serotype and its variants. For example, one vaccinia carrier virus can be used to carry AAV serotype 2 (AAV2) rep 78 and AAV serotype 9 (AAV9) vp2, another carrier virus can be used carry to AAV2 rep52 and AAV9 vp1 to produced pseudeotyped AAV9 vector. In a different embodiment, one vaccinia carrier virus can be used to carry AAV serotype 2 (AAV2) rep 78 and AAV serotype 1 (AAV1) vp2, another carrier virus can be used carry to AAV2 rep52 and AAV8 vp1 to produced pseudeotyped AAV vector with mixed AAV capsids which including AAV8 VP1, AAV8 VP3, AAV1 VP2 and AAV1 VP3.

It is also possible to express only VP1 and not VP3 from vp1 gene in the carrier vector by mutating the VP3 starting codon to other amino acids. Similar approach can be used to control VP3 expression from vp2 gene.

AAV capsid gene can be modified by DNA shuffling and genetic modification which can readily introduced by carrier viruses.

In another embodiment, the trans factor nucleic acid sequence comprises coding sequences for adenovirus E1a, E1b, E2a, E4ORF6 and/or VAI. In another embodiment, the helper functions are encoded by a single polycistronic transcript, and the promoter for the helper functions is a constitutive promoter, such as the vaccinia virus p7.5 promoter. In another embodiment, the carrier vector contains a vaccinia virus backbone and the coding sequences for adenovirus E2A and E4orf6. In a related embodiment, the coding sequences of adenovirus E2A and E4orf6 are separated by an internal ribosome entry site (IRES) and are under the control of a single vaccinia promoter.

In another embodiment, the carrier virus is a VSV. Since VSV has a relatively small genome, multiple VSVs may be needed to express all trans factors required for the production of a recombinant virus vector. In some situations, one or several key trans factors are expressed by VSV virus while other trans factors are expressed conventionally from the nucleus.

In some embodiments, two or more carrier vectors are introduced into the host cell. In other embodiments, a single carrier vector is used for the production of the recombinant virus vector.

The carrier virus can be constructed using methods well known in the art. In certain embodiments, the carrier virus is replication-competent in its native host cells but is replication deficient in the host cell for the recombinant virus vectors. For example, a vaccinia carrier virus is replication-competent in BSC, CV-1, and L cells, but is replication-deficient in the Hela cells which are used for the production of the recombinant virus vector of interest.

In certain embodiments, the carrier viruses are constructed with the vRB 12 virus backbone, which lacks the functional vp37 gene. The vRB 12-based carrier viruses propagate slowly in host cells that do not provide vp37 function, such as CV-1 cells, and extend the incubation period required for reaching cell lysis. This property can be used for the production of recombinant viral vectors when rapid cell lysis by vaccinia carrier virus is not desirable. For example, infecting Hela cells with a vaccinia carrier virus (at an MOI of 1) typically causes cell lysis at day 2 post infection. Infecting the same cells with a vRB12-based vaccinia carrier virus (vp37 deficient) would delay the cell lysis to day 3 or day 4 post infection. The extended incubation period provides more time for the production of the recombinant virus vectors in the host cell and increasing the recombinant vector yield. Alternatively, temperature sensitive mutants of vaccinia virus can also be used to control the time of host cell lysis.

Vaccinia virus will not productively infect CHO cells. However, cowpox virus can and if the cowpox host range gene is inserted into a vaccinia carrier virus, then the recombinant vaccinia carrier virus will infect CHO cells. The defect is at the stage of intermediate and late protein synthesis. Vaccinia virus also will not infect some lymphocyte lines and non-vertebrate cell lines. Such modification provides another way to control vaccinia virus replication and optimize the parameters for recombinant viral vector production.

In certain embodiments, one or more carrier vectors and/or carrier viruses may be constructed. The one or more carrier vectors and/or carrier viruses comprise all of the elements required to produce a replication-deficient recombinant viral vectors in a particular host cell or cell line. The number and type of elements that are required will depend upon the particular host cell used and the type of recombinant viral vectors to be produced.

Helper Functions Required for Recombinant AAV Production

The production of recombinant AAV typically requires helper functions from certain adenovirus proteins such as adenovirus E1a, E1b and E2a proteins, and probably adeonvirus E4ORF6 and VAI proteins as well. The helper functions may also be provided from the helicase-primase complex of herpes simplex virus (HSV) (e.g., UL5, UL8 and UL52), the major single-stranded DNA binding protein of HSV (UL29), products of all 7 HSV DNA replication genes (UL5, 8, 52, 29, 30, 9 and 42). The helper functions for recombinant AAV may also be provided by chemical or physical agents, including ultraviolet light, cycloheximide, hydroxyurea and various carcinogens. The helper functions may be provided by the host cell, or by a helper virus vector. The helper virus vector can be an adenovirus, an HSV, a cytomegalovirus (CMV), a vaccinia virus or pseudorabies virus (PRV). The helper functions may also be provided by a carrier virus.

The Recombinant Viral Genome (Cis Cassette)

The recombinant viral genome, or the "cis element," is resided in the nucleus of the host cell in either integrated form or episomal form. The recombinant viral genome cannot be excised, replicated, and packaged into virions without the trans factor(s) from the carrier virus vector. However, once the carrier virus infects the host cell hosting the recombinant viral genomes, the essential gene products required for replication and packaging of the recombinant viral genome will be expressed from carrier virus DNA in the cytoplasm. Because these essential gene products often have nucleus translocation signal. The mature proteins are then transported to the nucleus and meet the recombinant viral genomes, where the replication and packaging of recombinant viral DNA will take place. In this setting, the carrier vector DNA remains in the cytoplasm and does not meet the recombinant viral genome, which stays in the nuclei of the host cell. Therefore, the possibility of recombination between the recombinant viral vector genomes and carrier vector genomes, which may otherwise lead to the generation of replication competent viral particles, is reduced greatly or completely eliminated.

In certain embodiments, a recombinant viral genome may be inserted into a nucleus targeting vector and introduced into a host cell prior to, or concurrently with, the introduction of a carrier vector. The commonly used nucleus targeting vector include HSV or adenovirus. Lentiviral vector or retroviral vector may also be used to facilitate the integration of the cis cassette into the host chromosome.

In certain embodiments, the nuclear anchoring element is the EBV gene and the EBV origin. It has been shown that the anchoring effect of the EBV gene and the EBV origin is due to a high-affinity matrix attachment of the oriP sequence and an interaction of oriP with the origin binding protein, EBNA-1 (See e.g., Polvino-Bodnar and Schaffer, 1992, Virology 187, 591-603). In another embodiments, sv40 replication origin can also be used increase the copy number of the cis element.

The advantage of having the recombinant viral genome on a nucleus targeting vector is that it eliminates the need to establish a stable cell line that harbors the recombinant viral genome. The nucleus targeting vector would bring the recombinant viral genome into the nucleus of the host cell, thus achieve the goal of separating the recombinant viral genome from the carrier vector, which stays in the cytoplasm of the host cell.

The Host Cells

The host cell can be any cell that is infectible with a carrier virus. In certain embodiments, mammalian cell lines may be generated to facilitate the production of recombinant viral vectors. The cell lines stably express (either on an extrachromosomal episome or through integration in the cell's genome) certain trans factors and, in the case of AAV production, helper functions. For example, 293 cells (ATCC CRL-1573) constitutively produce adenoviral E1a and E1b proteins, which may serve as trans factors for the production of recombinant adenovirus or provide helper functions for the production of recombinant AAV. A stably transformed mammalian cell may provide some of the trans factor/helper functions, while other trans factor/helper functions are introduced into the cytoplasm of the host cell by a carrier virus.

Examples of the host cells include, but are not limited to, Hela cells, cos cells, BHK cells, A549 cells, and other primary or transformed T-cells, fibroblast cells, hepatocytes, endothelial cells, megkaryotcyes etc.

In certain embodiments, the host cell is a cell that is not receptive to the recombinant viral vector to be produced in the host cell, so that a host cell cannot be re-infected by the recombinant viral vector released by another lysed host cell. For example, human megakaryocytic leukaemia cell line, MB-02, Mo-7e, and myeloid cell line KG1, (Handa et al., J of Gen. Virol. 2000, 81, 2077-2084.) which are resistant to AAV serotype 2 infection but is susceptive to adenovirus and vaccinia virus infection, may be used as the host cell for the production of recombinant AAV with a vaccinia carrier virus.

In other embodiments, the host cells are cultured in suspension to improve the yield of the recombinant viral vectors. In other embodiments, the host cells are cells grown in an in vivo setting, such as hepatocytes in a mouse liver. The cells are infected in vivo by one or more carrier viruses and a nuclear target virus carrying a recombinant viral genome. The recombinant viral vectors are produced in vivo.

In certain embodiments, the host cell is a stably transformed call that expresses one or more proteins with helper functions or trans factors. In other embodiments, the method further includes introducing into the host cell a nuclear targeting vector containing a recombinant viral vectors genome. In a related embodiment, the nuclear targeting vector is a viral vector. In another embodiment, the nuclear targeting vector is an adenovirus vector. In yet another embodiment, the nuclear targeting vector is an adenovirus vector carrying a recombinant AAV genome.

The Replication-Deficient Recombinant Virus Vectors

The method of the present invention can be used for the production of any replication-deficient recombinant virus vector that replicates the viral genome in the nuclei of the host cells. Examples of such replication-deficient recombinant virus vectors include, but are not limited to, recombinant viruses of the Adenoviridae family, such as recombinant adenovirus vectors, recombinant viruses of the Herpesviridae family, such as herpes simplex virus (HSV) vectors, recombinant viruses of the Hepadnaviridae family, such as hepatitis B virus (HBV), recombinant viruses of the Parvoviridae family, such as AAV vectors, and any other DNA virus.

In certain embodiments, the replication-deficient recombinant virus vector is a viral vector from the Parvoviridae family, which includes viruses in the *Parvovirus* genus, such as LuIII virus and minute virus of mice (MVM), and viruses in the *Dependoviruses* genus, such as AAV. The method includes the steps of infecting a host cell with one or more carrier viruses, incubating the infected host cell for a desired period of time; and isolating the recombinant virus. The recombinant virus genome is introduced into the nucleus of the host cell by infecting the host with a recombinant adenovirus or herpes virus vector that carries the recombinant virus genome prior to the infection of the one or more carrier viruses.

Figure 3:
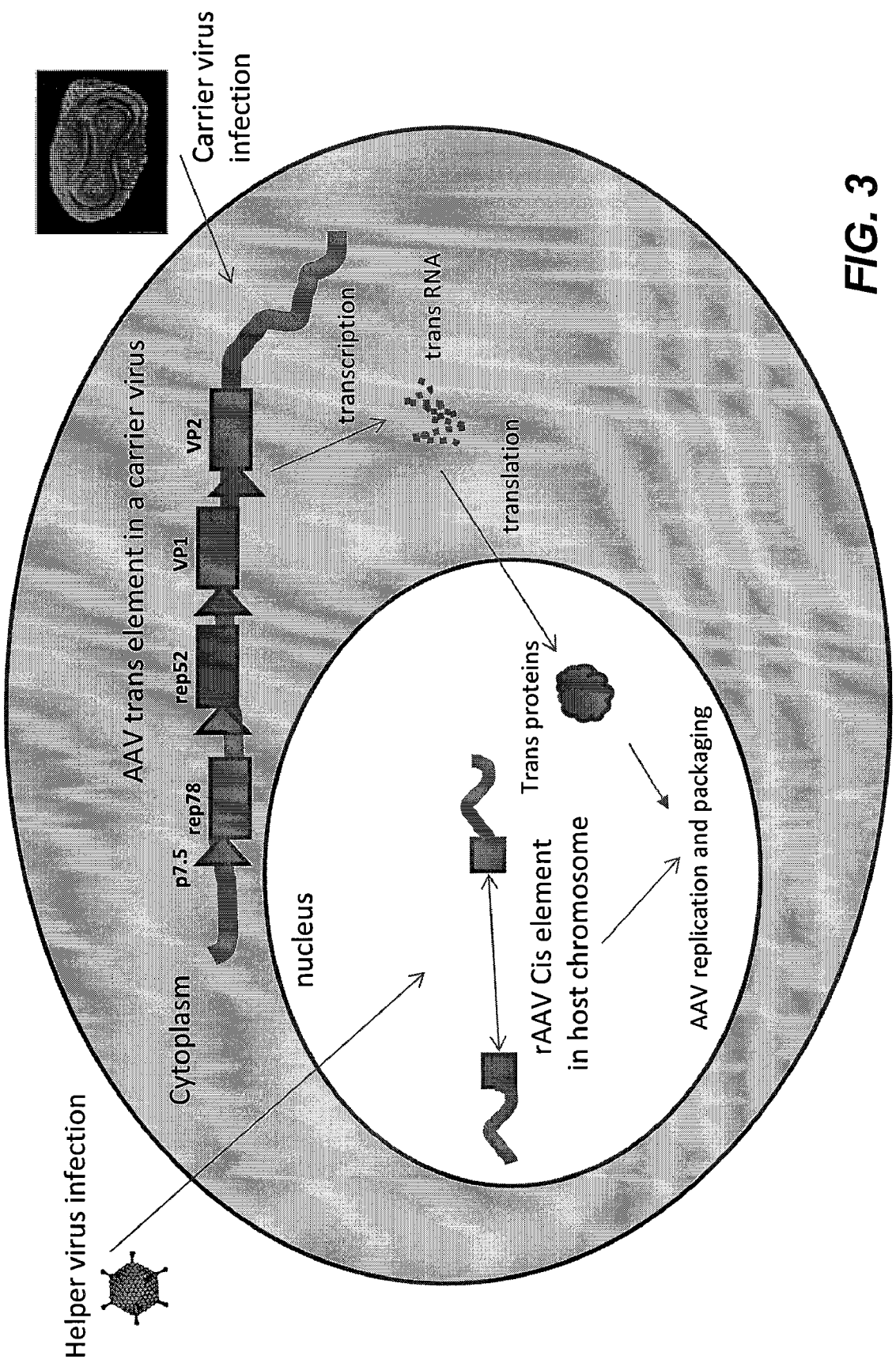
FIG. 3 is a diagram showing production of recombinant AAV vector using vaccinia virus as a carrier vector for the trans elements.

In a preferred embodiment, the replication-deficient recombinant virus vector is an AAV vector, and the one or more carrier viruses carry the coding sequence for a capsid protein of AAV. The one or more carrier viruses can be a single virus, a mixture of several viruses of the same type (e.g., several vaccinia carrier viruses each carrying a different trans factors), or a mixture of different types of viruses (e.g., a vaccinia virus carrying a VP1 and a VSV carrying Rep78). In a preferred embodiment, the carrier viruses are vaccinia viruses. In a more preferred embodiment, a single vacinnia carrier virus carrying the AAV rep78, rep 52, vp1 and vp2 genes is used for the production of the recombinant AAV. FIG. 3 is a diagram showing production of recombinant AAV vector using vaccinia virus as a carrier vector for the trans elements.

Figure 4:
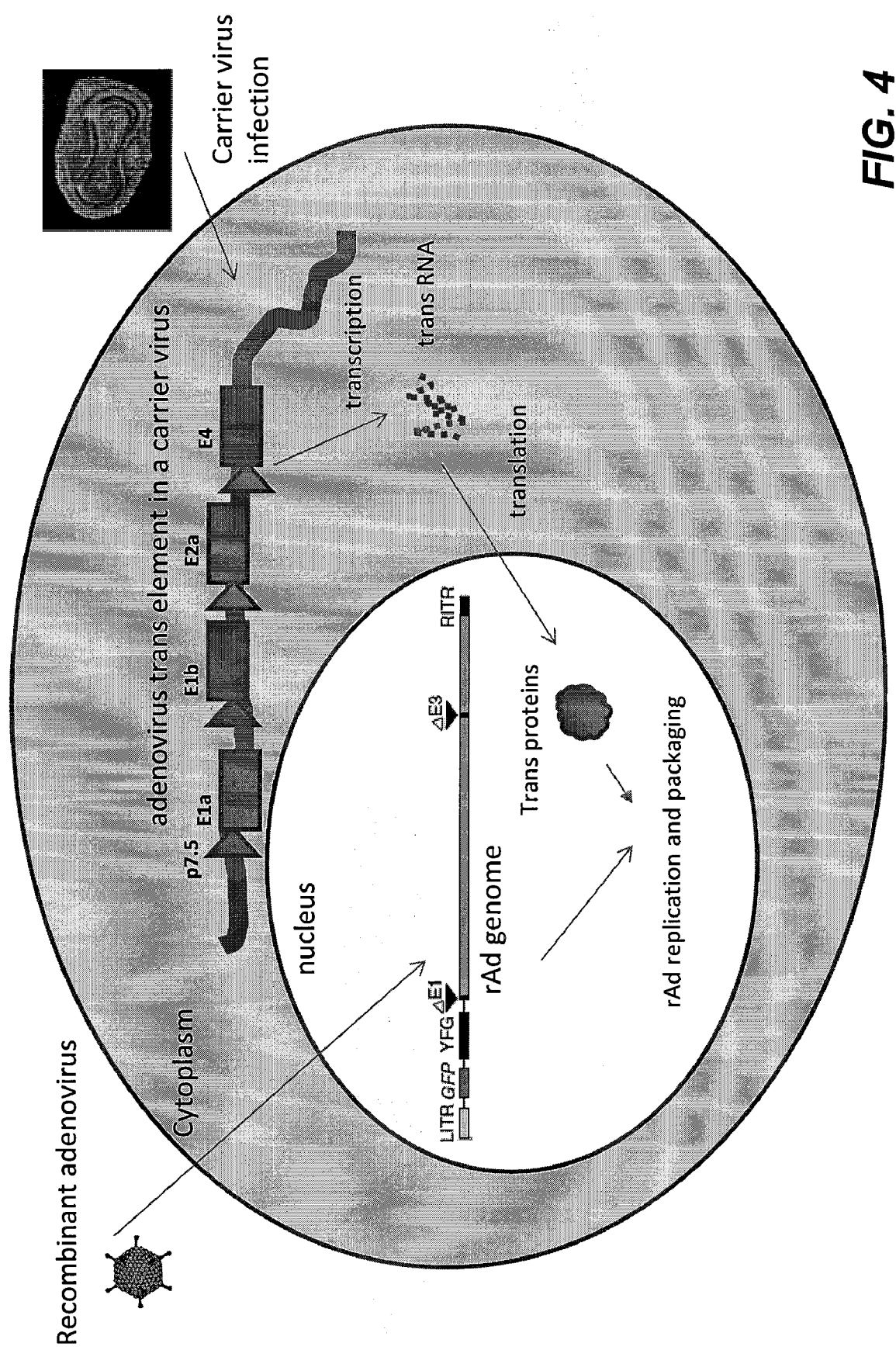
FIG. 4 is a diagram showing production of recombinant adenovirus vector using vaccinia virus as a carrier vector for the trans elements.

In other embodiments, the replication-deficient recombinant virus vector is an adenovirus vector. Examples of recombinant adenoviral vectors include, but are not limited to, E1-deleted adenoviral vectors, E1- and E2-deleted adenoviral vectors, E1-, E2- and E4-deleted adenoviral vectors, and gutless adenovirus vectors. FIG. 4 is a diagram showing production of recombinant adenovirus vector using vaccinia virus as a carrier vector for the trans elements. Since the trans factors carried by the carrier virus may vary, all known adenovirus vectors can be produced in this way which includes but not limited to E1, E3 deleted adenovirus vectors, E1, E2, E3, and E4 deleted adenovirus vectors and gutless adenovirus vectors.

Figure 5:
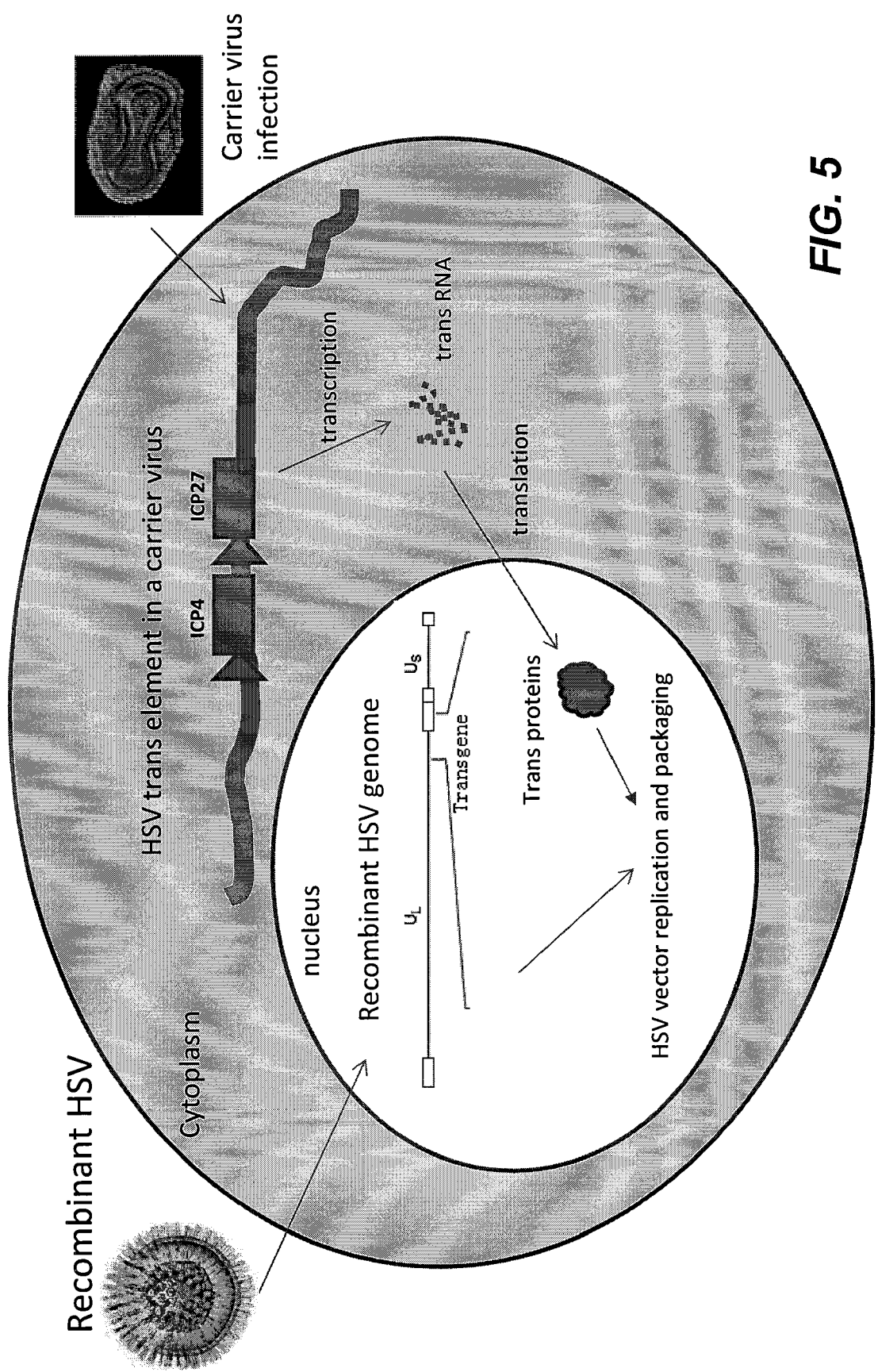
FIG. 5 is a diagram showing production of gutted adenovirus vector using vaccinia virus as a carrier vector for the trans elements.

In other embodiments, the replication-deficient recombinant virus vector is a HSV vector. FIG. 5 is a diagram showing production of recombinant HSV vector using vaccinia virus as a carrier vector for the trans elements. In another embodiments, HSV-1 amplicon vectors can be produced by supplied ICP4, ICP27 by a carrier virus and the rest helper genes by cosmids.

Figure 6:
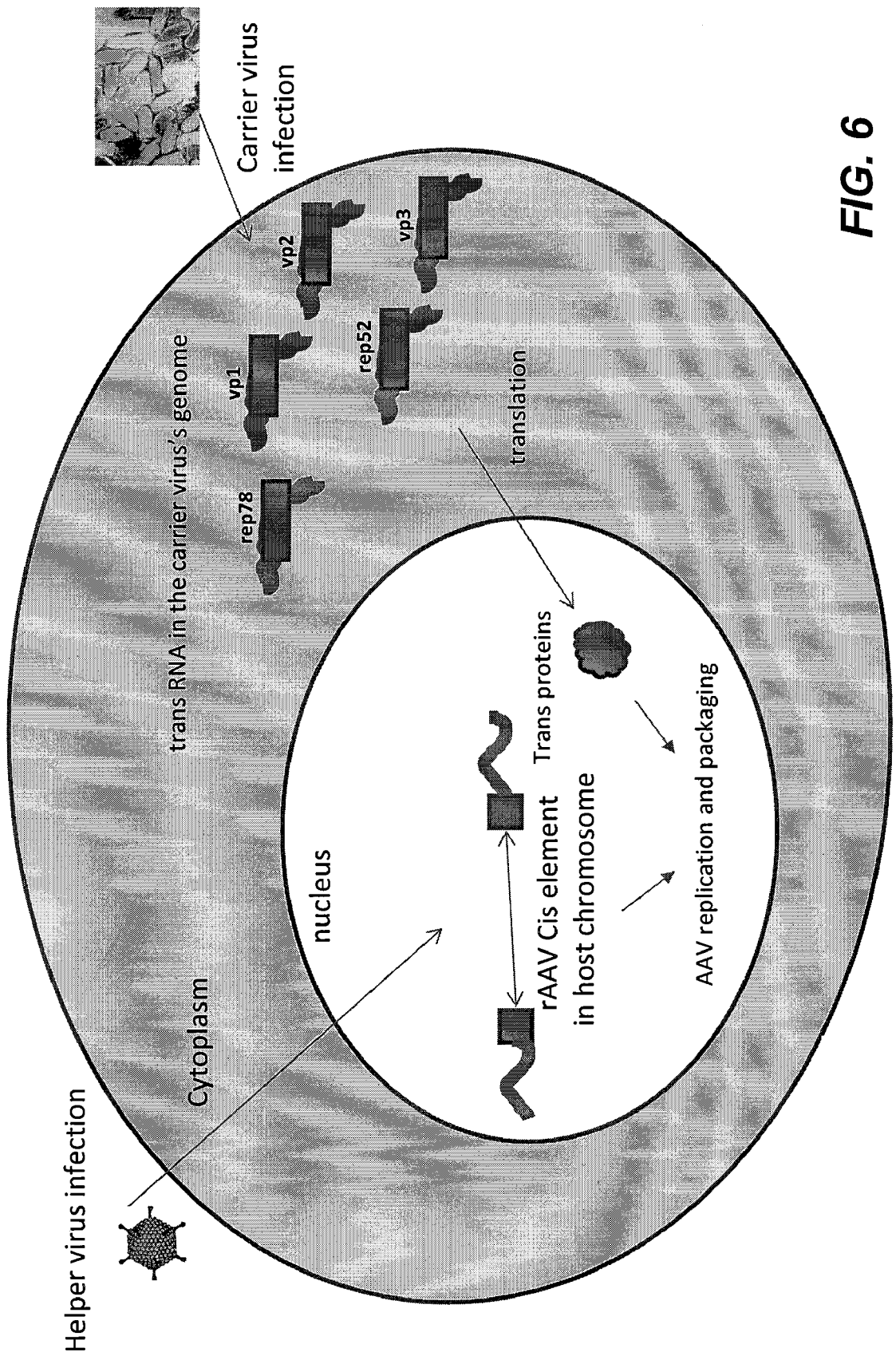
FIG. 6 is a diagram showing production of recombinant AAV vector using VSV virus as carrier vectors for the trans elements.

In other embodiments, the replication-deficient recombinant virus vector is an AAV vector. FIG. 6 is a diagram showing production of recombinant AAV vector using VSV as carrier vectors for the trans elements.

Infection of the Host Cell with the Carrier Virus

Infection of the host cells by the carrier virus(s) is carried out under conditions suitable for the particular carrier virus/host cell combination. The infection conditions (e.g., cell density, multiplicity of infection, composition of the infection medium, infection temperature, etc.) can be determined by one skilled in the art based on the host cell type and the characteristics of the viruses used for the infection.

In certain embodiments, the host cells may be transfected or infected with a nucleus targeting vector prior to the infection of the carrier viruses, incubated for a desired period of time to allow the nucleus targeting vector to enter the nuclei of the host cell, and then infected with the carrier virus. The length of the incubation period can be determined experimentally depending on the type of host cell and the type of nucleus targeting vector. In one embodiment, the host cells are first infected with the recombinant adenovirus-based nucleus targeting vector or HSV-based nucleus targeting vector carrying the a recombinant viral genome, and then infected with the carrier virus with the required trans factor(s) after an incubation period of about 6-24 hours, about 8-18 hours, about 10-14 hours, or about 12 hours.

In certain embodiment, the host cells are infected with an adenovirus-based nucleus targeting vector carrying a recombinant AAV genome. The adenovirus-based nucleus targeting vector can be any adenovirus that is capable of providing the helper function required for the production of the recombinant AAV in the host cell. Examples of such adenoviruses include, but are not limited to, first generation adenovirus with deletion in E1a, E1b, $2^{nd}$ generation or third generation of adenovirus with more deletions. Besides human adenovirus, non human primate adenovirus or adenovirus from other species can also be used.

Isolation of Recombinant Virus Vectors

Methods for isolation of recombinant viral vectors from host cells are well known in the art. General methods include centrifugation or ultracentrifugation with CsCl gradient or sucrose gradient, or iodixanol gradient, filtration (e.g., using a 0.22 μm filter), chromatography or combinations thereof. Methods for purifying recombinant AAV vectors are described, for example, in Current Protocols in Human Genetics, UNIT 12.9 Production of Recombinant Adeno-Associated Viral Vectors by Vivian W. Choi, Aravind Asokan, Rebecca A. Haberman, and Richard Jude Samulski. Methods for purifying recombinant adenovirus vectors are described, for example, in Current Protocols in Human Genetics, UNIT 12.4, Adenoviral Vectors, by Tong-Chuan He,; UNIT 12.13, Helper-Dependent Adenoviral Vectors, by Kazuhiro Oka, Lawrence Chan. Methods for purifying recombinant HSV vectors are described, for example, in Current Protocols in Human Genetics, UNIT 12.11, Construction of Replication-Defective Herpes Simplex Virus Vectors, by William F. Goins, Peggy Marconi, David Krisky, Darren Wolfe, Joseph C. Glorioso, Ramesh Ramakrishnan, and David J. Fink,; UNIT 12.12, Gene Delivery Using Helper Virus-Free HSV-1 Amplicon Vectors, by Cornel Fraefel.

If a vaccinia virus is used as the carrier virus, the vaccinia carrier virus particles can be easily removed from the lysate of host cells by filtration. If the host cells are cultured in a suspension culture, recombinant viruses may be harvested from the supernatant of the culture medium. In certain embodiments, recombinant AAV vectors produced using vaccinia carrier viruses are purified by lysing the host cells, removing large cellular debris by centrifugation and passing the centrifugation supernatant through a 0.22 µm filter to remove carrier virus.

In certain embodiments, recombinant AAV vectors prepared by the method of the present invention are isolated using as described column chromatography by Gao et al. (Hum Gene Ther. 2000, 11:2079-2091).

Another aspect of the present invention relates to a replication-deficient recombinant viral vectors produced using the method of the present invention. The recombinant DNA viruses produced with method of the present invention is free from replication-competent viral particles. As used herein a virus that is "free from replication-competent viral particles" refers to a replication-deficient recombinant virus stock that (1) contains no detectable level of replication-competent virus, or (2) contains replication-competent virus at a level that is below a threshold level.

In certain embodiments, the recombinant DNA virus free from replication-competent viral particles is a replication-deficient recombinant AAV stock that contains no detectable replication-competent viral particles or a replication-deficient recombinant AAV stock that contains replication-competent viral particles at a level below one replication-competent viral particle out of every $10^{10}$ recombinant viral particles, every $10^{11}$ recombinant viral particles, every $10^{12}$ recombinant viral particles, or every $10^{13}$ recombinant viral particles.

In other embodiments, the recombinant DNA virus free from replication-competent viral particles is a replication-deficient recombinant adenovirus stock that contains no detectable replication-competent viral particles or a replication-deficient recombinant adenovirus stock that contains replication-competent viral particles at a level below one replication-competent viral particle out of every $10^9$ recombinant viral particles, every $10^{10}$ recombinant viral particles, every $10^{11}$ recombinant viral particles, or every $10^{12}$ recombinant viral particles.

In other embodiments, the recombinant DNA virus free from replication-competent viral particles is a replication-deficient recombinant HSV stock that contains no detectable replication-competent viral particles or a replication-deficient recombinant HSV stock that contains replication-competent viral particles at a level below one replication-competent viral particle out of every $10^7$ recombinant viral particles, every $10^8$ recombinant viral particles, every $10^9$ recombinant viral particles, or every $10^{10}$ recombinant viral particles.

Methods for detecting replication-competent recombinant virus particles in a stock of replication-deficient recombinant virus are well established in the field of art. Examples of such methods include, but are not limited to, Southern blot analysis of wild type virus genomes or ELISA/Western blot analysis of viral particles after multiple rounds of amplification under permissive replication conditions for wild type virus. Such methods have been described, for example, by Allen et al. (J. Virol. 1997, 71:6816-6822) (detection of replication-competent AAV particles), Marzio et al. (Vaccine, 2007, 25:2228-2237 (detection of replication-competent adenovirus particles), and Goins et al. (Methods Mol Biol. 2008, 433:97-113 (detection of replication-competent HSV particles).

Another aspect of the present invention relates to a carrier virus for the production of a replication-deficient recombinant viral vectors based on single stranded or double stranded DNA viruses. The carrier virus contains in its genome a cytoplasmic virus backbone and a nucleotide sequence encoding one or more trans factors required for the production of a replication-deficient recombinant virus vector.

In certain embodiments, the nucleotide sequence encoding one or more trans factors encodes a structure protein of the replication-deficient recombinant virus vector.

In other embodiments, the nucleotide sequence encoding one or more trans factors encodes one or more AAV capsid proteins. In one embodiment, the carrier virus is a vaccinia carrier virus carrying one or more nucleotide sequence encoding AAV capsid proteins. In another embodiment, the carrier virus is a vaccinia carrier virus carrying the AAV vp1 and vp2 genes, each gene is controlled by its own promoter.

In other embodiments, the carrier virus is a vaccinia carrier virus carrying one or more nucleotide sequence encoding adenovirus E1a, E1b, E2a and/or E4ORF6 proteins.

In other embodiments, the carrier virus is a vaccinia carrier virus carrying one or more nucleotide sequence encoding HSV ICP4 and ICP27 proteins.

EXAMPLES

Example 1

Construction of Vaccinia Carrier Viruses Carrying Adenovirus Genes

Figure 7:
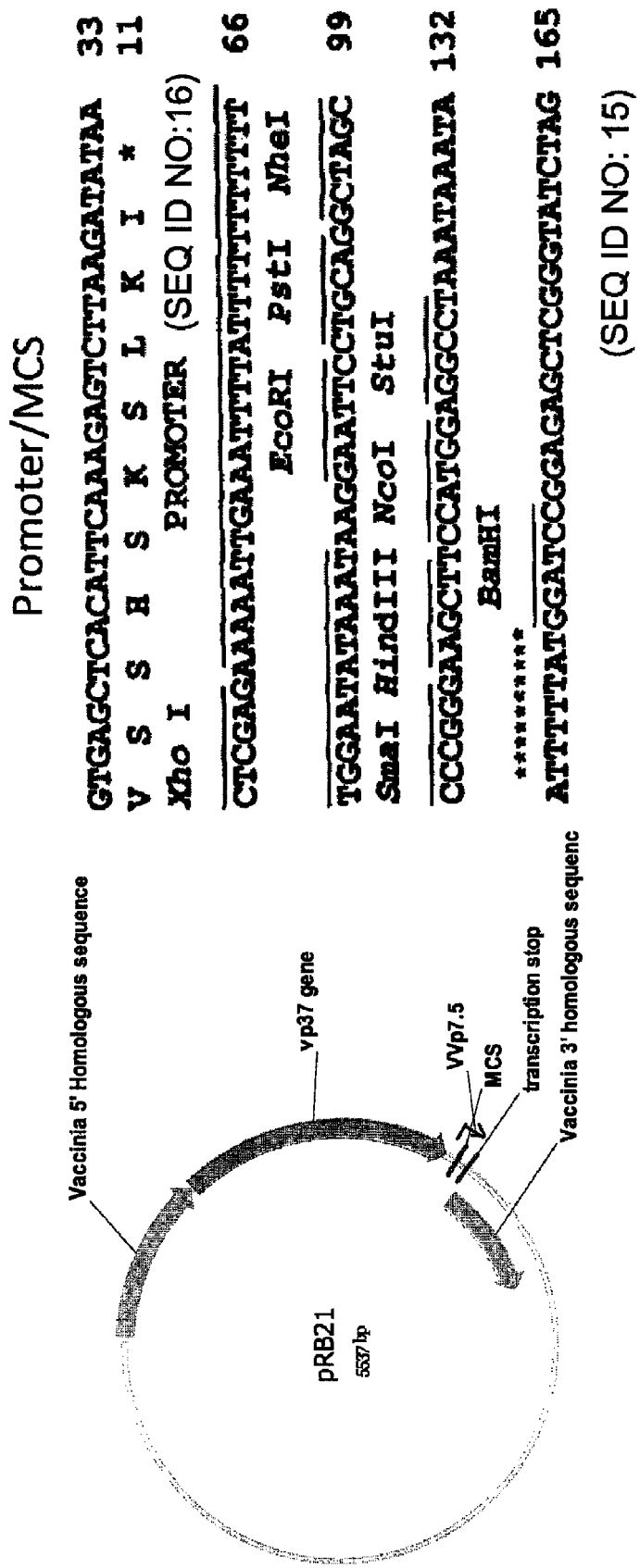
FIG. 7 is a map of shuttle plasmid pRB21.

The adenovirus cDNA gene, E1a, E1b, E2a, E4ORF6 are PCR amplified and cloned into plasmid vector Prb21 (Blasco and Moss, Gene, 1995, 158:157-162) in the MCS behind the vaccina virus p7.5 promoter. FIG. 7 shows a plasmid map of pRB21, including the nucleotide sequence of the promoter/multiple cloning site (MCS) region (SEQ ID NO:15). The resulting shuttle plasmids, designed pRB-E1a, pRB-E2b, pRB-E2a, pRB-E4ORF6, are then transfected into BSC cells and infected with vaccinia virus vRB12 (supra). The vRB12 virus lacks the gene encoding protein VP37. pRB21 provides a complete copy of the VP37 gene, thus allowing recombinant vaccinia virus to be selected on the basis of plaque formation. The carrier virus clone which expressed these gene products were then picked and amplified as described by Blasco and Moss (supra).

Example 2

Construction of Vaccinia Carrier Viruses Carrying HSV Genes

The cDNA for HSV ICP4 and ICP27 are PCR amplified and cloned into pRb21 in the MCS behind the p7.5 promoter. The resulting shuttle plasmids pRB21-ICP4 and pRB21-ICP27 were then transfected into BSC cells and infected with vRB12. The carrier virus clone which expressed hepes gene were then picked and amplified as described in Example 1.

Example 3

Construction of Vaccinia Carrier Viruses with AAV Genes

Figure 8:
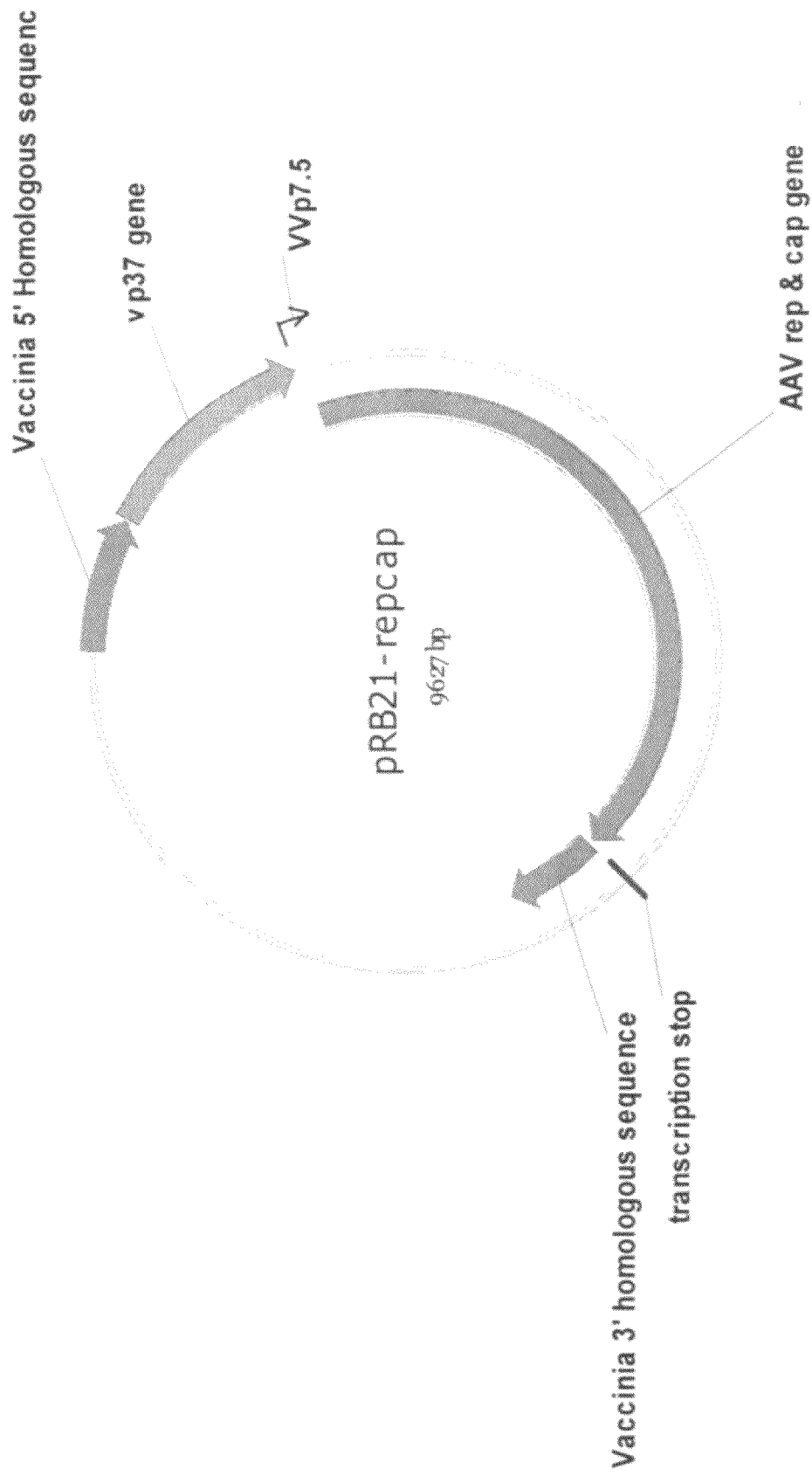
FIG. 8 is a map of shuttle plasmid pRB-repcap.

AAV rep and cap gene were PCR amplified from the ATG of rep78 to the stop codon of VP3 and cloned into pRb21 behind the p7.5 promoter (SEQ ID NO:1). The resulting shuttle plasmids, designated pRB-repcap (FIG. 8), was then transfected into BSC cells and infected with vRB12. The carrier virus clone which expressed AAV genes were then picked and amplified as described in Example 1. The resulting vaccinia carrier virus is named vvAAVRepcap. Western blot analysis showed that vvAAVrepcap mainly expressed Rep78. There are no cap proteins expressed. It demonstrated that each gene of AAV has to be specially cloned in order to provide proper gene expression.

Figure 9:
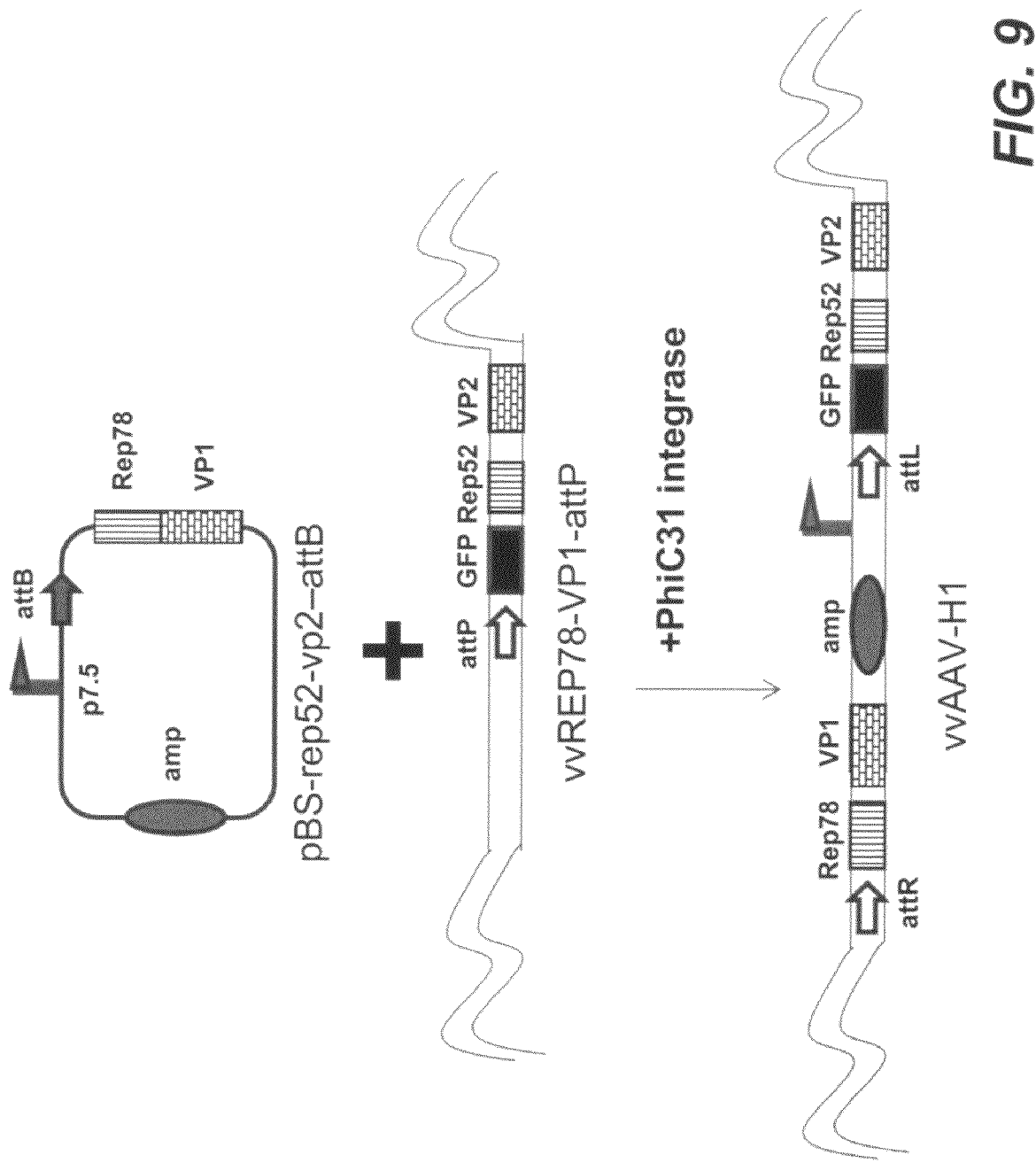
FIG. 9 is a diagram showing the construction of vvAAV-H1.

AAV rep78, rep 68, rep52, rep40, vp1, vp2 and vp3 genes were PCR amplified. The amplified genes were individually cloned into pRb21 behind the p7.5 promoter. The resulting shuttle plasmids, designated pRB-rep78, pRB-rep68, pRB-rep52, pRB-Rep40, pRB-vp1, pRB-vp2 and pRB-vp3 were then transfected into BSC cells and infected with vRB12. The carrier virus clone which expressed the AAV genes were then picked and amplified as described in Example 1. The resulting vaccinia carrier viruses are designated vvAAVrep78, vvAAVrep68, vvAAVrep52, vvAAVRep40, vvAAVvp1, vvAAVvp2 and vvAAVvp3, respectively. The sequences of the trans cassettes in these viruses are shown in SEQ ID NO:2 (rep78 expression cassette), SEQ ID NO:3 (rep68 expression cassette), SEQ ID NO:4 (rep52 expression cassette), SEQ ID NO:5 (rep40 expression cassette), SEQ ID NO:6 (vp1 expression cassette), SEQ ID NO:7 (vp2 expression cassette) and SEQ ID NO:8 (vp3 expression cassette), To construct a single vaccinia carrier virus expressing rep78, rep52, VP1, VP2 and VP3 for recombinant AAV production (rep68 and rep40 are not necessary for recombinant AAV production), a vaccinia carrier virus expressing Rep78 and VP1 was constructed first. Briefly, both rep78 and vp1 genes were cloned into pRB21 under their own p7.5 promoters to generate shuttle plasmid pRB-rep78vp1-attP (FIG. 9). As shown in FIG. 9, a phage attachment (attP) site was also included in the shuttle plasmid. The rescued vaccinia carrier virus was named vvREP78-VP1-attP.

The second shuttle vector was constructed using pBluecript-SK+ as the backbone. Rep52 and VP2 under their own p7.5 promoter were cloned into pBluescript-SK+ along with a phage attachement (attB) site. The resulting shuttle plasmid is designated pBS-rep52-vp2-attB. After BSC cells were transfected with pBS-rep52-vp2-attB and expressing plasmid for phiC37 integrase, the cells were infected with vvREP78-VP1-attP, the resulting vaccinia carrier virus, which carries AAV rep78, rep52, vp1 and vp2 genes, is designated as vvAAV-H1 (FIG. 9).

Example 4

Expression of AAV Capsid Protein by Vaccinia Carrier Viruses

The rescued carrier viruses were tested for their ability to express the AAV genes carried in the viral genome. Briefly, vvAAVrep78, vvAAVrep68, vvAAVrep52, vvAAVRep40, vvAAVvp1, vvAAVvp2 and vvAAVvp3 were respectively used infect Hela cells at a MOI of 1. The cell lysates were collected at 48 hours post-transfection and antibodies specific for AAV2 capsid protein were used to Western blot detection of capsid proteins.

Figure 10:
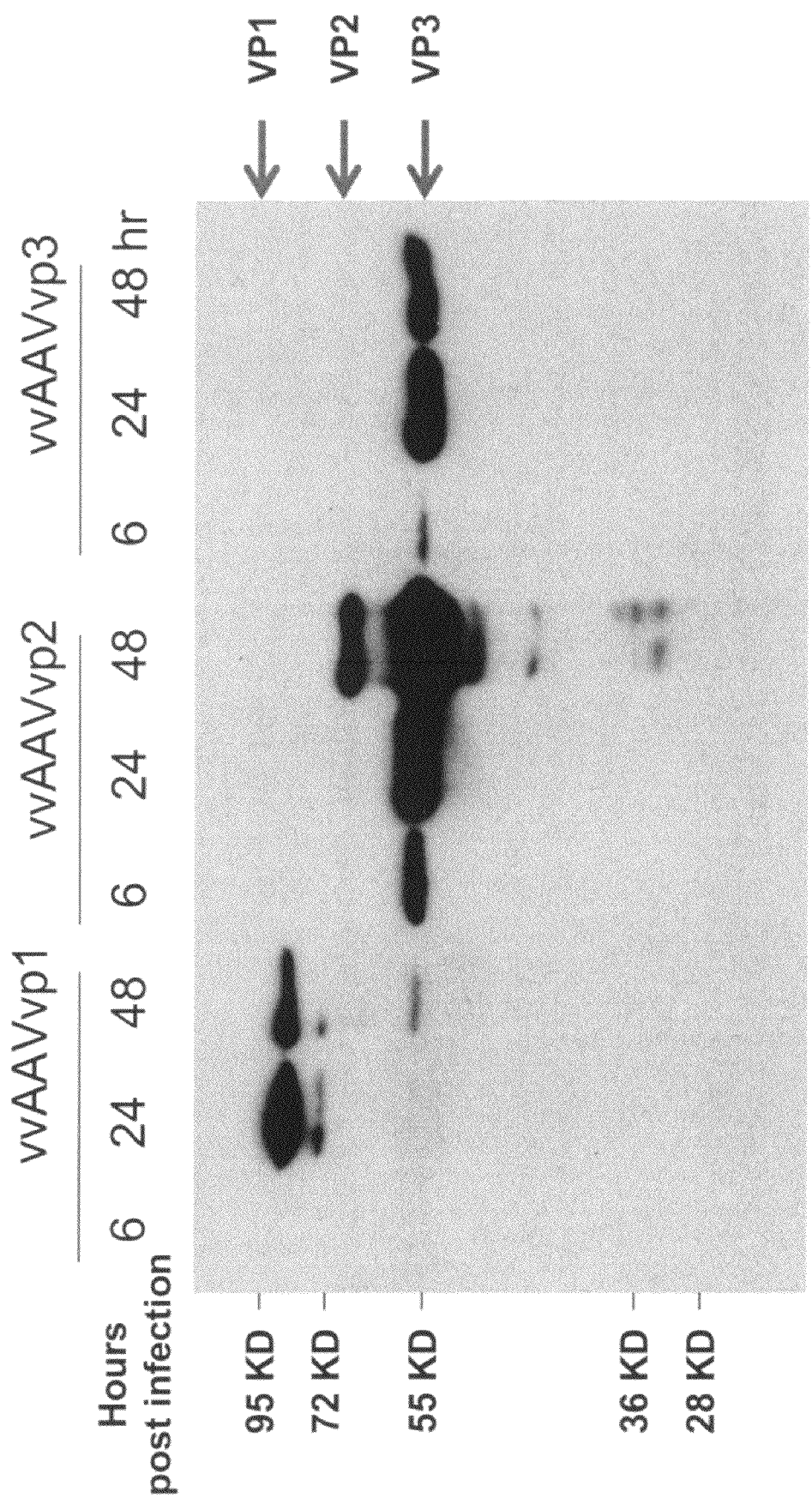
FIG. 10 is a picture of a Western blot showing the expression profile of vvAAVvp1, vvAAVvp2 and vvAAVvp3 in HeLa cells using antibodies specific for VP1, VP2 and VP3.

The Western blots revealed vvAAVrep78, vvAAVrep68, vvAAVrep52, vvAAVRep40 expressed rep78, rep68, rep52 and rep40 respectively. vvAAVvp3 expressed only VP3. However, vvAAVvp1 expresses both VP1 and VP3. The expression of VP3 is minor. vvAAVvp2 expresses both VP2 and VP3. VP3 is a major component. This is shown in the FIG. 10.

In wild type AAV virus, three capsid genes vp1, vp2 and vp3 overlap each other. A single P40 promoter allows all three capsid proteins to be expressed at a ratio of 1:1:10, which complement with rAAV production. Although the vaccinia carrier virus vvAAVvp1 has the cassette for VP1, VP2 and VP3 under the control of p7.5 promoter, the western blot analysis showed that only VP1 and VP3 were expressed. However, the VP1, VP2, VP3 proteins are expressed at a ratio (1:1:10) suitable for AAV production when vvAAVvp1, vvAAVvp2 infects the HeLa cells at a ratio of 1:1.

Example 5

Construction of Nucleus Targeting Vectors Carrying AAV ITR-CMV-GFP

The recombinant AAV genomes including two copy of AAV ITR and a GFP expression cassette containing a CMV promoter, the GFP gene and a polyadenylation site were cloned into the pShuttle plasmid (Invitrogen, Life Technologies Corp., Carlsbad, Calif.). Adenovirus vector carrying AAV ITR-CMV-GFP were then rescued out with pAdeasy kit (Invitrogen, Life Technologies Corp., Carlsbad, Calif.), and purified as described in Current Protocols in Human Genetics, UNIT 12.4, Adenoviral Vectors, by Tong-Chuan He. The vector was named as vAd-AAVITR-CMV-GFP. It is used to deliver AAVITR-CMV-GFP sequence to the nucleus of the cells.

Example 6

Figure 11:
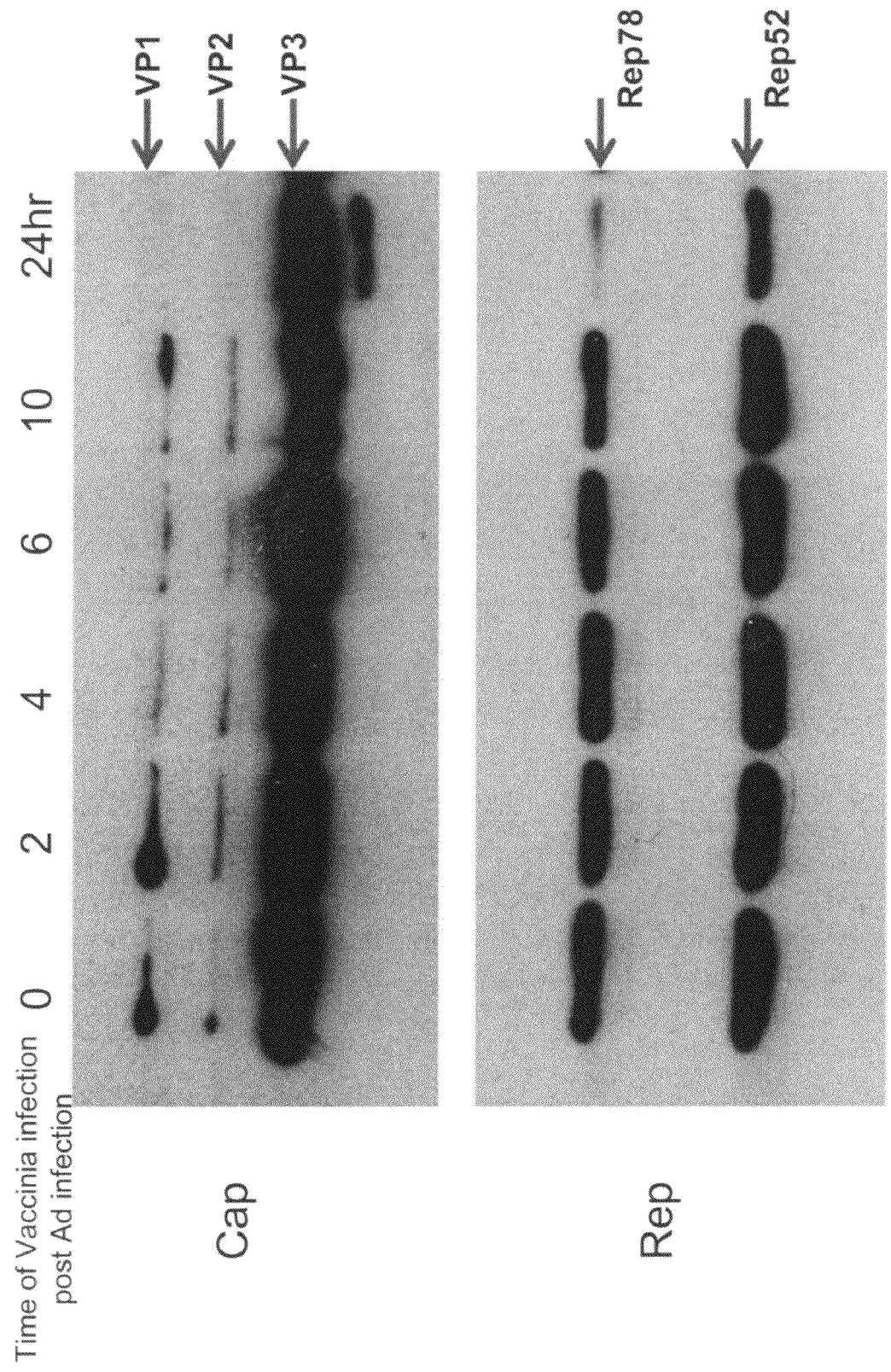
FIG. 11 is a diagram showing the expression profile of Rep and Cap in an AAV production example. First vAd-AAVITR-CMV-GFP infected HeLa cells at an MOI=2, then 5 rVVs (vvAAVrep78, vvAAVrep52,vvAAVvp1, vvAAVvp2, vvAAVvp3) each infected the HeLa cells at an MOI=1 at different time points indicated in the Figure. The HeLa cells were collected after 48 hr rVVs transduction. Shown in the Figure is the western blot for cap and rep expression from the harvested cell lysates.

Production of Recombinant AAV Using Vaccinia Carrier Viruses and vAd-AAVITR-CMV-GFP Hela cells were infected first with vAd-AAVITR-CMV-GFP at a multiplicity of infection (MOI) of 2, then with a mixture of equal amount of vvAAVrep78, vvAAVrep52, vvAAVvp1, vvAAVvp2, and vvAAVvp3 at an MOI of 1 at 12 hours post-vAd infection. An example of the rep and cap expression profile is shown FIG. 11. The cells were harvested 36 hours after vvAAV virus infection. The recombinant AAV (i.e., rAAV-CMV-GFP) was purified from the cell lysate using the ultracentrifugation with CsCl gradient as described by Current Protocols in Human Genetics, UNIT 12.9 Production of Recombinant Adeno-Associated Viral Vectors, by Choi et al.

In another experiment, Hela cells were infected first with vAd-AAVITR-CMV-GFP at a multiplicity of infection (MOI) of 2, then with a mixture of equal amount of vvAAVrep78, vvAAVrep52, vvAAVvp1, and vvAAVvp2 at an MOI of 1 at 12 hours post-vAd infection. The cells were harvested 36 hours after vvAAV virus infection. The recombinant AAV (i.e., rAAV-CMV-GFP) was purified from the cell lysate using the ultracentrifugation with CsCl gradient as described by Current Protocols in Human Genetics, UNIT 12.9 Production of Recombinant Adeno-Associated Viral Vectors, by Choi et al.

In another experiment, Hela cells were first infected with vAd-AAVITR-CMV-GFP, then infected with vvAAV-H1 at 12 hours post-vAd infection at MOI of 2. The cells were harvested 36 hours after vvAAV virus infection. The recombinant AAV was purified from the cell lysate as described in Current Protocols in Human Genetics, UNIT 12.9 Production of Recombinant Adeno-Associated Viral Vectors, by Choi et al.

Example 7

Remove Vaccinia Carries from Recombinant Vector Preparations

Since Vaccinia virus is significant larger than other DNA viruses, it can be filtered from recombinant viral vector preparations by filtering the vectors through a 0.22 um filter.

Example 8

Production of Recombinant AAV Using Vaccinia Carrier Viruses and Cell Line with Integrated Recombinant AAV Genomes Hela cells were stably transfected with pAAV-CMV-GFP. The resulting cell line, designated as Hela-AAV-CMV-GFP, was infected with either vvAAV-H1 or a combination of vvAAVrep78, vvAAVrep52, vvAAVvp1, vvAAVvp2, vvAAVvp3. The cell lysate containing recombinant AAV genomes were collected at 36 to 48 hours post infection. The recombinant AAV was purified from the cell lysate as described in Example 6.

Example 9

Production of Recombinant AAV Using Vaccinia Carrier Viruses and Cell Line with Recombinant AAV Genomes Existing as Episomes in the Nucleus AAVITR and CMV-GFP was cloned into the pRep4 vector (Invitrogen, Life Technologies Corp., Carlsbad, Calif.), which contains EBNA and EBV latent origin and remains as episomes in the nucleus of the cells. The resulting plasmid, designated pRep4-AAV-CMV-GFP, was transfected into Hela cells. Hygromycin was added to the transfected cells to select cells with desired number of episomes. The selected cells were then infected with either vvAAV-H1 or a combination of vvAAVrep78, vvAAVrep52, vvAAVvp1, vvAAVvp2, vvAAVvp3. The cell lysate containing recombinant AAV genomes were collected at 36 to 48 hours post infection. The recombinant AAV was purified from the cell lysate as described in Example 6.

In this case, adenovirus helper function would improve the yield of recombinant AAV vectors, but the adenovirus helper function is not required for the generation of rAAV vectors.

Example 10

Production of Recombinant AAV Using Vaccinia Carrier Viruses In Vivo in Animal Liver vvAAVrep78, vvAAVrep52, vvAAVvp1, vvAAVvp2, vvAAVvp3 and vAd-AAVITR-CMV-GFP are injected intravenously into immunodeficient Rag-1 mice. The liver of the mice are harvested 48 hours after virus infection. The recombinant AAV particles are purified from the liver tissue as described in Current Protocols in Human Genetics, UNIT 12.9: Production of Recombinant Adeno-Associated Viral Vectors, by Choi et al Alternatively, vvAAV-H1 and vAd-AAVITR-CMV-GFP are injected intravenously into immunodeficient Rag-1 mice. The liver of the mice are harvested 48 hours after virus infection. The recombinant AAV particles are purified from the liver tissue as described in Example 6.

The in vivo production of recombinant AAV requires no tissue culture reagent and equipment, and can easily scale up by using larger animals.

Example 11

A Model for Continuous rAAV Production

A cell line that is non-permissive for AAV infection, such as human megakaryocytic leukaemia cells (MB-02), is used for rAAV production. Briefly, MB-02 cells are infected with vvAAV-H1 and vAd-AAVITR-CMV-GFP in a suspension culture. The cells supernatant is harvested continuously. Fresh cells are added periodically. The recombinant AAV particles are purified from the harvested supernatant.

The advantage of this system is that the recombinant AAV particles released from the cells cannot re-enter the host cells and are released into the supernatant. This approach would greatly improve the yield of recombinant AAV production.

Example 12

Use of VSV Vector for AAV Vector Production

The vaccinia carrier vectors described in Examples 1-10 can be replaced by VSV carrier vectors VSV-rep78, VSV-Rep-52, VSV-VP1, VSV-VP2 and VSV-Vp3. Since VSV is a cytoplasmic RNA virus, it would prevent recombinantion between the recombination of rAAV genome and AAV functional genome sequences, which eliminate replication competent AAV particles formation. VSV carrier viruses can be generated as described by Miller et al., Protein Expr Purif. 2004, 33:92-103.

Example 13

Vaccinia Carrier Vector for Adenovirus Vector Production

In this example, vaccinia carrier virus is used to express some necessary genes for adenovirus production. Vaccinia carrier vector carrying adenovirus E1a, E1b and E4 genes will be generated as described in Example 1. Hela cells will be co-infected with recombinant adenovirus and vv-E1aE1bE4. The helper function provided by the vaccinia carrier virus would allow replication of the rAd in the Hela cells. The Hela cells will then be lysed and the recombinant adenovirus purified as described in Example 5. This system would allow quick production of recombinant adenovirus vector without the contamination of replication-competent adenovirus. The sequence for the trans cassette expressing human Ad5 E1a gene is shown in SEQ ID NO:9. The sequence for the trans cassette expressing human Ad5 E1b 55k gene is shown in SEQ ID NO:10. The sequence for the trans cassette expressing human Ad5 E2a gene is shown in SEQ ID NO:11. The sequence for the trans cassette expressing human Ad5 E4 gene is shown in SEQ ID NO:12.

Example 14

Vaccinia Carrier Virus for Replication-Deficient HSV Vector Production

Because the HSV immediate early (IE) genes contribute to the toxicity of the virus, it is necessary to sequentially delete these cytotoxic genes from the viral vector genome. In addition, deletion of multiple genes from the virus increases the amount of foreign DNA that can be incorporated into the vector. Conventionally, in order to construct replication-defective genomic HSV type 1 (HSV-1) mutant vectors, it is necessary to first produce a cell line capable of synthesizing the IE gene product(s) required to complement the deletion virus. Our approach to elimination of the homologous recombination between the deletion virus and the HSV-1 gene is to express these essential early genes in vaccinia virus instead of a complementing cell line.

In this example, vaccinia carrier viruses are constructed to express genes necessary for hepesvirus production. In one embodiment, vaccinia carrier vectors carrying HSV-1 IE (ICP4 and ICP27) genes under the control vaccinia p7.5 promoter are generated using pRB21 plasmid, vRB12 virus and BSC cells as described above. The resulting vaccinia vectors are designated vvICP4-27. The recombinant herpes vector lacks the above genes but carrying CMV-GFP (vHerp-GFP) can be generated following the protocol described in Current Protocols in Human Genetics, UNIT 12.11 "Construction of Replication-Defective Herpes Simplex Virus Vectors" by William F. Goins et al. updated on Jan. 14, 2010. The sequence for the trans cassette expressing human HSV-1 ICP4 gene is shown in SEQ ID NO:13. The sequence for the trans cassette expressing human HSV-1 ICP27 gene is shown in SEQ ID NO:14. To grow the HSV vectors in large scale, vvICP4-27 and vHerp-GFP were used to infect vero cells at a MOI of 2. After adsorption, decant the inoculum and add 100 to 125 ml complete MEM/10% FBS per bottle. Incubate at 37° C. until all the cells have rounded up and are starting to detach from the surface. The HSV vector vHerp-GFP were then purified using the protocol described in the Current Protocols in Human Genetics, UNIT 12.11 "Construction of Replication-Defective Herpes Simplex Virus Vectors" by William F. Goins et al., updated on Jan. 14, 2010.

Similarity, the vaccinia carrier virus can also be adapted for production of HSV amplicon vector. Cornel Fraefel, UNIT 12.12, Gene Delivery Using Helper Virus-Free HSV-1 Amplicon Vectors, Current Protocols in Human Genetics.

Example 15

Production of Recombinant Parvovirus MVM Vector Using Vaccinia Carrier Viruses and Cell Lines with Integrated Recombinant MVM Genomes NBK (human newborn kidney cell line) cells were stably transfected with pMVM-100a as described by Brandenburger et al. (Hum Gene Ther. 1999, 10:1229-1238). The positive clone (NBK-MVM-100a) with full recombinant MVM genome will be used for vector production. vvMVM-NS1, vvMVM-NS2, vvMVM-VP1 and vvMVM-VP2 will be constructed respectively to express NS1, NS2, VP1 and VP2 proteins. NBK-MVM-100a will infected with the above-described four viruses at a MOI of 1 for each virus. The cell lysate containing recombinant MVM genomes were collected at 36 to 48 hours post infection. Recombinant parvovirus MVM vector will be isolated as described as described by Brandenburger and Velu,. J Gene Med. 2004,6 Suppl 1: S203-11.

Example 16

RCA Level in rAAV Vectors Preparation Using a Vaccinia Carrier Virus

Human 293 cells were seeded at either $2.5 \times 10^5$ cells per T-25 flask or $5 \times 10^6$ cells per 10-cm-diameter dish. The next day, the cultures were infected with adenovirus (MOI=5) and infected with vector or wt AAV. After 72 h, either the cells were harvested and episomal DNA was isolated by the method of Hirt or the cells were scraped into the medium, subjected to three cycles of freeze-thaw in a dry ice-ethanol bath, and centrifuged to pellet the cell debris. The clarified crude lysate was incubated at 56° C. for 1 h to inactivate the adenovirus, and 500 ml was added to a fresh plate of 293 cells with or without fresh adenovirus (MOI 5 5) for a second round of amplification. After an additional 72 h, the cells were scraped into the medium and pelleted, and total genomic DNA was prepared by standard techniques (31). The DNA was subjected to Southern analysis and hybridized with either a 32P-labeled BglII fragment from pAV2 comprising the entire AAV2 genome or a HindIII/SnaBI fragment of pAV2 containing the cap sequence.

The rAAV produced in example 6 showed that RCA were undetectable from $1 \times 10^{11}$ particles.

It should be noted that the above-described virus production can be done in suspension cells, since the carrier virus vector can infect host cells easily. In addition, since vaccinia virus has a diameter of about 0.23~0.4 μm, it can be conveniently removed from the recombinant viral vectors by filtering through a 0.22 μm column.

This invention thus has many advantages over current methods for manufacturing recombinant viral vectors. These advantages include: (1) the cytoplasm carrier viruses such as vaccinia virus has a large genome (about 300 kb) that permits insertion of large DNA sequences without compromising the efficiency of recombinant viral vectors production; (2) the cytoplasmic carrier viruses will not meet the recombinant vector genome and therefore there will be no recombination events leading to the regeneration of replication competent viral particles; and (3) some cytoplasm carrier viruses, such as vaccinia virus, have a large size and can be easily removed from recombinant viral vector preparations; and (4). The methods of the present invention are particularly suitable to large scale production of replication-deficient recombinant viral vectors since the time-consuming transfection based methods could be eliminated.

The herein described compositions and methods may be used to produce various recombinant viral vectors. The disclosure references particular means, materials and embodiments. Although the claims make reference to particular means, materials and embodiments, it is to be understood that the claims are not limited to these disclosed particulars, but extend instead to all equivalents.

What is claimed is:

1. An isolated cytoplasmic carrier virus, comprising:

a nucleotide sequence encoding one or more capsid proteins (VP1, VP2 and VP3) and one or more other structural proteins of an adeno-associated virus (AAV), wherein said nucleotide sequence encoding one or more capsid proteins comprising one or more mutations at its original initiation codon from ATG to ACG or vice versa to assure a suitable ratio for production of a recombinant AAV vector, and wherein said nucleotide sequence is constructed to express said capsid and other structural proteins in the cytoplasmic compartment upon a host cell is infected with said carrier cytoplasmic virus.

2. The carrier virus of claim 1, wherein said carrier virus is a vaccinia carrier virus or vesicular stomatitis virus (VSV), and wherein said virus genome comprises an expression cassette having an AAV VP1 gene under a control of a vaccinia virus p7.5 promoter when the cytoplasmic carrier virus is a vaccinia virus.

3. The carrier virus of claim 1, wherein said cytoplasmic carrier virus genome further comprises:

a nucleotide sequence that encodes one or more AAV non-structure proteins or variants thereof.

4. The carrier virus of claim 2, comprising a first expression cassette having an AAV VP1 gene under the control of a first vaccinia virus p7.5 promoter and a second expression cassette having an AAV VP2 gene under the control of a second vaccinia virus p7.5 promoter.

5. The carrier virus of claim 1, wherein said cytoplasmic carrier virus is a member of poxviridae family.

6. method for producing a replication-deficient recombinant AAV vector, said method comprising:

infecting a host cell with one or more cytoplasmic carrier viruses of claim 1, wherein said cytoplasmic carrier viruses are cytoplasmic viruses that encode two or more AAV capsid proteins and express said two or more capsid proteins in the cytoplasm of said host cell in a ratio suitable for a production of said replication-deficient recombinant AAV vector;

incubating the infected host cell for a desired period of time; and isolating said replication-deficient recombinant virus vector.

7. The method of claim 6, wherein said cytoplasmic carrier virus is a vaccinia virus or vesicular stomatitis virus (VSV).

8. The method of claim 6, wherein said two or more AAV capsid proteins are expressed under a control of vaccinia virus p7.5 promoter.

9. The method of claim 7, wherein said two or more AAV capsid proteins comprise VP2 and VP3 proteins expressed from a first vaccinia cytoplasmic carrier virus and a VP1 protein expressed from a second vaccinia cytoplasmic carrier virus.

10. The method of claim 7, wherein the infecting step comprises infecting said host cell with a single vaccinia cytoplasmic carrier virus that expresses AAV VP1, VP2 and VP3 proteins at a ratio suitable for the production of said replication-deficient AAV vector.

11. The method of claim 10, wherein said single vaccinia cytoplasmic carrier virus contains a first expression cassette having AAV VP1 gene under a control of a first vaccinia virus p7.5 promoter and a second expression cassette having AAV vp2 gene under a control of a second vaccinia virus p7.5 promoter.

12. The method of claim 6, wherein said cytoplasmic carrier virus is a member of poxviridae family.

* * * * *